(12) United States Patent
Amir et al.

(10) Patent No.: US 9,591,983 B2
(45) Date of Patent: Mar. 14, 2017

(54) WEARABLE FETAL MONITORING SYSTEM HAVING TEXTILE ELECTRODES

(71) Applicant: HEALTHWATCH LTD., Herzliya (IL)

(72) Inventors: Uri Amir, Or Yehuda (IL); Oleg Malafriev, Rehovot (IL); Itzhak Katz, Petach Tikva (IL)

(73) Assignee: HEALTHWATCH LTD., Herzeliya (IL)

( * ) Notice: Subject to any disclaimer, the term of this patent is extended or adjusted under 35 U.S.C. 154(b) by 0 days.

(21) Appl. No.: 14/892,538

(22) PCT Filed: Jun. 1, 2014

(86) PCT No.: PCT/IL2014/050493
§ 371 (c)(1),
(2) Date: Nov. 19, 2015

(87) PCT Pub. No.: WO2014/192002
PCT Pub. Date: Dec. 4, 2014

(65) Prior Publication Data
US 2016/0128594 A1 May 12, 2016

Related U.S. Application Data

(60) Provisional application No. 61/830,077, filed on Jun. 1, 2013, provisional application No. 62/006,102, filed on May 31, 2014.

(51) Int. Cl.
*A61B 5/0205* (2006.01)
*A61B 5/08* (2006.01)
(Continued)

(52) U.S. Cl.
CPC ............. *A61B 5/0448* (2013.01); *A41D 1/20* (2013.01); *A61B 5/01* (2013.01); *A61B 5/021* (2013.01);
(Continued)

(58) Field of Classification Search
CPC ..... A61B 5/0205; A61B 3/113; A61B 5/0022; A61B 5/7267
(Continued)

(56) References Cited

U.S. PATENT DOCUMENTS 4,781,200 A    11/1988    Baker
6,970,731 B1 *    11/2005    Jayaraman ........... A61B 5/0008
                                                                                        600/388

(Continued)

FOREIGN PATENT DOCUMENTS

AU       2008208376 A1    7/2008
WO      2012102040 A1    8/2012

(Continued)

OTHER PUBLICATIONS

Fanelli, Andrea et al., "Prototype of wearable system for remote fetal monitoring during pregnancy," 32nd Annual International Conference of the IEEE EMBS, 2010, 5815-5818), Buenos Aires, Argentina.

(Continued)

*Primary Examiner* — Carl H Layno
*Assistant Examiner* — Jon Eric C Morales
(74) *Attorney, Agent, or Firm* — Troutman Sanders LLP

(57) ABSTRACT

A seamless, smart fetal monitoring garment and methods of using thereof. The system includes a knitted or interwoven garment having a multiplicity of conductive textile electrodes for sensing maternal and fetal electrical vital signals. The maternal and fetal electrical vital signals are selected from a group including maternal heart rate, fetal heart rate and electromyogram (EMG) activities including uterine activities. The method includes wearing the garment, acquiring electrical mixed common, maternal and fetal vital signals from surface region of a pregnant woman, using the plurality of textile electrodes, optimally weighted summing- (Continued)

up the acquired signals, analyzing the summed-up signals to thereby extract the maternal signal and the fetal signal, including determining their heart rates, and including detecting health hazards and in some embodiments, including detecting a uterine contraction sequence suggesting the need to be hospitalized for birth giving.

21 Claims, 20 Drawing Sheets

(51) Int. Cl.
  *A61B 5/145* (2006.01)
  *A61B 5/0448* (2006.01)
  *A41D 1/20* (2006.01)
  *A61B 5/024* (2006.01)
  *A61B 5/0452* (2006.01)
  *A61B 5/0488* (2006.01)
  *A61B 5/01* (2006.01)
  *A61B 5/021* (2006.01)
  *A61B 5/0472* (2006.01)
  *A61B 5/11* (2006.01)
  *A61B 5/00* (2006.01)

(52) U.S. Cl.
  CPC ...... *A61B 5/02055* (2013.01); *A61B 5/02411* (2013.01); *A61B 5/0452* (2013.01); *A61B 5/0472* (2013.01); *A61B 5/0488* (2013.01); *A61B 5/0816* (2013.01); *A61B 5/11* (2013.01); *A61B 5/14542* (2013.01); *A61B 5/6804* (2013.01); *A61B 5/6805* (2013.01); *A61B 5/7203* (2013.01); *A61B 5/746* (2013.01); *A61B 5/002* (2013.01); *A61B 5/0006* (2013.01); *A61B 5/0011* (2013.01); *A61B 2503/02* (2013.01); *A61B 2562/0209* (2013.01); *A61B 2562/04* (2013.01)

(58) Field of Classification Search
  USPC ........................................ 600/345, 309, 364
  See application file for complete search history.

(56) References Cited

U.S. PATENT DOCUMENTS

| 8,340,748 | B2 | 12/2012 | Kimura et al. | |
|---|---|---|---|---|
| 2005/0267376 | A1 | 12/2005 | Marossero et al. | |
| 2005/0267377 | A1* | 12/2005 | Marossero | A61B 5/02411 600/511 |
| 2005/0277841 | A1 | 12/2005 | Shennib | |
| 2007/0255184 | A1 | 11/2007 | Shennib | |
| 2008/0045808 | A1 | 2/2008 | Hassonjee et al. | |
| 2008/0091097 | A1* | 4/2008 | Linti | A41D 13/1281 600/389 |
| 2011/0259638 | A1 | 10/2011 | Sherrill et al. | |
| 2012/0123232 | A1* | 5/2012 | Najarian | A61B 5/0022 600/345 |
| 2013/0102857 | A1 | 4/2013 | Wolfberg et al. | |
| 2016/0000374 | A1* | 1/2016 | Dandekar | A61B 5/0002 600/301 |

FOREIGN PATENT DOCUMENTS

| WO | 2012106219 A1 | 8/2012 |
|---|---|---|
| WO | 2014002823 A1 | 1/2014 |

OTHER PUBLICATIONS

Fanelli et al., "Telefetalcare: a first prototype of a wearable fetal electrocardiograph," 33rd Annual International conference of the IEEE, EMBS, Boston, MA, USA, Aug. 30-Sep. 3, 2011, pp. 6899-6902.
Extended European Search Report for EP Application No. EP16174201 Dated Dec. 7, 2016, 13 pages.
International Search Report for International Application No. PCT/IL2013/050963 Dated Sep. 28, 2014, 4 pages.
Taralunga, et al., "Abdominal Signals: Denoising by Application of the Event Synchrunuous Canceller," Proceedings of Ihe 29th Annual International Conference of the IEEE EMBS, Cité Internationale, Lyon, France, Aug. 23-26, 2007, pp. 566-569.
Ungureanu, et al., "The event synchronous canceller algorithm removes maternal ECG from abdominal signals without affecting the fetal ECG," Computers in Biology and Medicine, vol. 39, No. 6, Jun. 1, 2009, pp. 562-567.

* cited by examiner

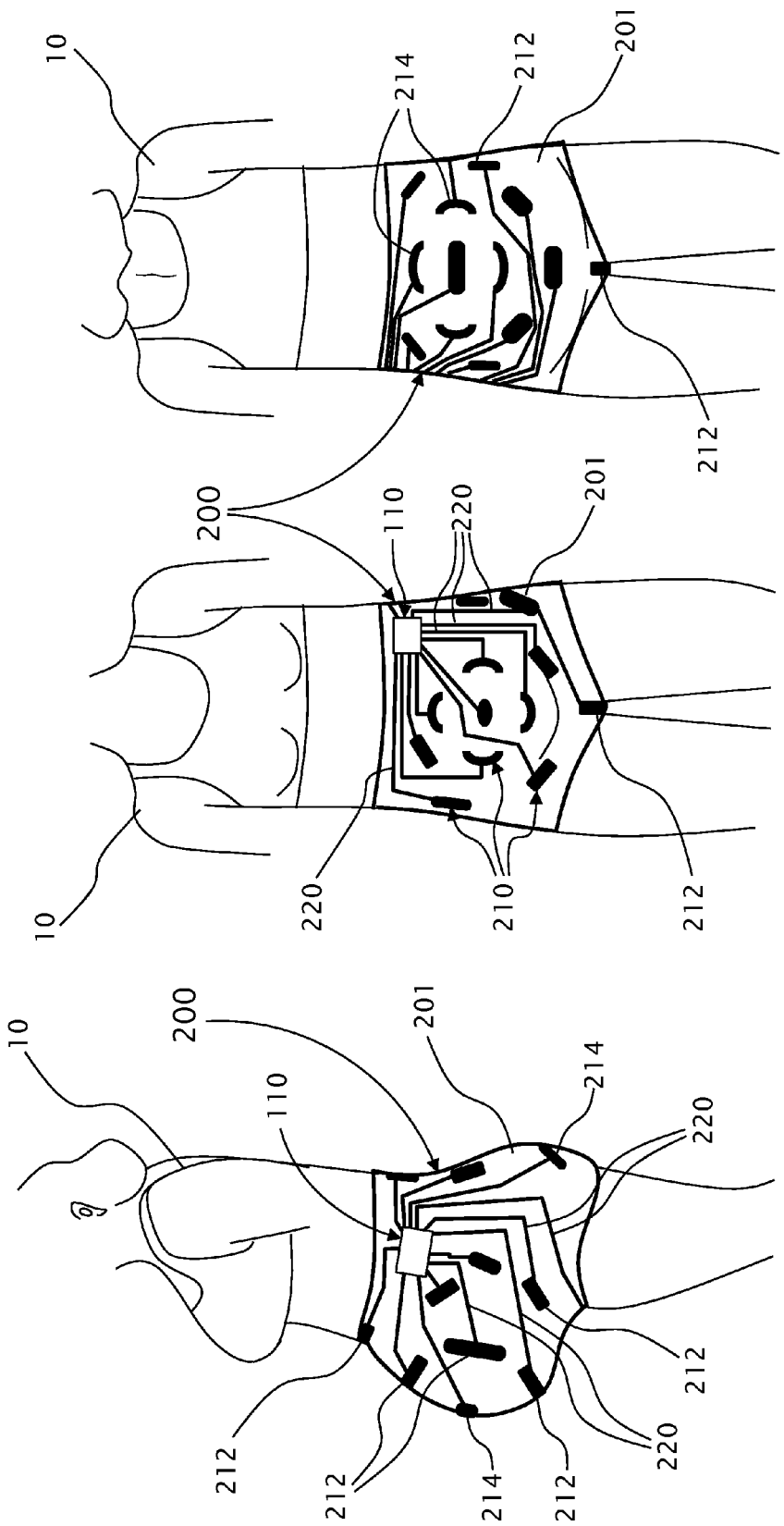

WEARABLE FETAL MONITORING SYSTEM HAVING TEXTILE ELECTRODES

CROSS REFERENCE TO RELATED APPLICATIONS

This application is a United States national stage entry of an International Application serial no. PCT/IL2014/050493 which claims the benefit under 35 USC 119(e) from U.S. provisional application 61/830,077 filed Jun. 1, 2013, the disclosures of which are included herein by reference.

This application further claims the benefit under 35 USC 119(e) from U.S. provisional application 62/006,102 filed May 31, 2014, the disclosures of which is included herein by reference.

This application also related to PCT application PCT/IL2013/050963, filed Nov. 23, 2013, entitled "Vertical conductive textile traces and methods of knitting thereof", and PCT application PCT/IL2013/050964, filed Nov. 23, 2013, entitled "Float loop textile electrodes and methods of knitting thereof", all of which are incorporated herein by reference as if fully set forth herein

FIELD OF THE INVENTION

The present invention relates to real-time health monitoring systems and more particularly, the present invention relates to a real-time, fetal monitoring system that can be comfortably worn by a monitored pregnant woman, by wearing a special garment, having at least one textile electrode embedded within the garment. The unique textile electrode is configured to detect fetal activity regardless of the position of the fetus within the mother.

BACKGROUND OF THE INVENTION AND PRIOR ART

Electrocardiogram (ECG) monitoring has been widely used on people for detecting medical conditions, such as abnormities associated with the heart. Signals representing a monitored person's cardiac activities can be collected through external electrodes distributed over the person's body. Typically, electrodes are attached to the skin of the chest and limbs of the monitored person.

Monitoring of fetal ECG is performed to detect Fetal Distress Syndrome, an abnormal condition during gestation or at the time of delivery marked by altered heart rate or rhythm and leading to compromised blood flow or changes in blood chemistry.

High-risk pregnancies are increasingly prevalent given the higher age at which women become pregnant and the ability to achieve pregnancies in women with high-risk comorbidities. Approximately 20-25% of all pregnancies are complicated to some degree, involving complications such as preterm delivery, fetal oxygen deficiency, fetal growth restriction and hypertension. Currently, there is no seamless, non-obtrusive monitoring system to continuously detect deviations in health status of the pregnant woman or the fetus.

The most prominent method for monitoring of the fetal health condition is monitoring of heart rate variability in response to activity of the uterus, using cardiotocography (CTG). Despite its high sensitivity, the specificity of CTG is relatively low. Generally, in obstetrical practice, the heart rate is determined using a non-invasively (Doppler) ultrasound probe on the maternal abdomen or invasively, using an electrode fixed onto the fetal scalp. The first method is relatively inaccurate, but is applicable throughout the pregnancy. The latter method is far more accurate but can only be applied following rupture of the membranes and sufficient dilatation, restricting its applicability to only the very last phase of pregnancy.

Monitoring of the fetal electrocardiogram (ECG), as a supplement of CTG, may increase the accuracy of detecting fetal distress. Currently, fetal ECG can be measured reliably by means of an invasive scalp electrode. Attempts to record the fetal ECG non-invasively from the maternal abdomen have been hampered by the low signal to noise ratio (SNR) of the transabdominal ECG, although several gel-based, non-seamless, and obtrusive commercial products are available. The abdominal ECG tracings are also dependent on position of the fetus within the maternal uterus.

Monitoring of fetal ECG can be difficult due to a number of reasons. One problem is the co-existence of maternal and fetal signals in raw signals acquired from a monitored person, as well as the relatively low fetal signal level relative to the maternal signal and other noise sources. Another problem is the current position of the fetus and motion of the fetus.

Also, typically, either a physician or a nurse is responsible for the actual placement of the electrodes at the specific points known to be adequate for accurate ECG measurements. Typically, the placement of the electrode involves attaching the electrodes such that is can be only forcibly removed. Furthermore, typically, to obtain a signal that can be decoded, the electrode must be applied on a moist surface, typically using gel. Alternatively, dry attaching electrodes, such as provided by Orbital Research are used in the art. However, typically, both types require skin preparations such as cleaning and shaving hairy skin.

There is therefore a need and it would be advantageous to have a real-time, fetal monitoring system that can be comfortably worn by a monitored pregnant woman. The special garment includes at least one textile electrode, preferably embedded within the garment, which textile electrode is configured to detect fetal activity regardless of the position of the fetus within the mother. The garment and/or the textile electrodes are either knitted or interwoven.

The term "continuous monitoring", as used herein with conjunction with a health monitoring system, refers to a health monitoring system, facilitated to monitor a living being substantially and continuously, day and night, when the monitored living being is awake or asleep, and active in substantially all common activities of such living being.

The term "seamless", as used herein with conjunction with a wearable device, refers to a device that when worn by an average person, wherein the device imposes no significant limitation to the normal life style of that person and preferably not seen by anybody when used and not disturbingly felt by the user while wearing it. Furthermore, no activity is required from the monitored person in order for the system to provide data and a personal-alert when needed. As the "seamless" characteristics refers also to the user's behavior, the wearable component is preferably an item that is normally worn (e.g., underwear) and not some additional item to be worn just for the purpose of monitoring.

The terms "underwear", or "leotard", or "garment", as used herein with conjunction with wearable clothing items, refers to seamless wearable clothing items that preferably, can be tightly worn adjacently to the body of a monitored pregnant woman, typically adjacently to the skin, including underwear, underpants, leotard and the like.

The term "tightly" means that specific portions of the garment where there are electrodes or other sensors that require certain pressure on the body to obtain a satisfactory signal, are designed to be as tight as needed. However, all the other parts of the garment may be not as tight. Optionally, there is a provision to facilitate tightening or releasing certain portions of the garment, by built-in straps or other tightening means, so that the need for more or less tightness does not require the replacement of the whole garment.

The term "abnormal", as used herein with conjunction with health related parameters, refers to a parameter value or one or more ranges of values which are defined as health hazardous or as potential health hazardous, when a trend is identified, and requires attention. For example, the normal blood pressure of an adult person is in the range 120/80 mm Hg. Typically, a systolic blood pressure of 130 mm Hg would not be considered hazardous. However, if a person has a stable mean blood pressure of around 85±10 mm Hg, and suddenly it increases to 125±10 mm Hg, this may be considered as an abnormal situation. Likewise, if the mean blood pressure changes gradually and consistently from 85 mm Hg to 120 mm Hg, in a clear trend, a personal-alert should be issued. The threshold value from which the high blood pressure parameter is considered as health hazardous may vary and can be set personally and optionally, dynamically updated, either manually or automatically, by an adaptation algorithm. Once the high blood pressure parameter, in the hereinabove example, is set, any value out of the set threshold value will then be considered as abnormal for that person.

BRIEF SUMMARY OF THE INVENTION

The principal intentions of the present invention include providing a fetal monitoring system that can be comfortably worn by a monitored pregnant woman, by wearing a special garment, having at least one textile electrode embedded within the garment. The textile electrode is configured to detect fetal heart electrical activity, electrical and/movement activity, regardless of the position of the fetus within the mother.

The smart garment with a multiplicity of textile electrodes is capable of measuring the heart rate of the fetus and preferably, also the heart rate of the mother. Optionally, the smart garment with textile electrodes is also capable of measuring at least one of the following maternal parameters: oxygen saturation, respiratory rate, skin temperature, blood pressure, ECG parameters such as ST elevation and depression, and body posture and movement.

For heart rate determination of the pregnant woman, at least one electrode is used. Respiratory rate can be measured using impedance technology, for example. Oxygen saturation can be measured using a sternal pulse oximeter with reflectance technology, for example. Blood Pressure may be determined, for example, from the Oxygen saturation and ECG parameters analyzed together. Body posture and movement can be determined using, for example, an accelerometer embedded in the processor or pressure sensors, for example textile pressure sensors knitted into the smart garment For heart rate determination of the fetus, at least two electrodes are used, disposed at the lower abdomen of the mother. In addition, textile electrodes, capable of detecting mechanical pressure imposed on the woman's abdomen, may be embedded into the garment. Thus, continuous monitoring of fetal heart rate and uterine contractions (CTG) can be achieved.

The signals collected are transmitted by dedicated yarn, embedded in the smart garment, to a processor, preferably connected to the garment using a proprietary docking station snapped onto the garment. The processor processes and analyzes the signals, using a specifically designed algorithm. Resulting relevant data is then transmitted, typically using wireless communication means such as Wi-Fi or Bluetooth, to a coupled target device, such as a smartphone or to a preselected center for further medical supervision and instruction.

According to the teachings of the present invention, there is provided a seamless, smart maternal monitoring garment including a tubular form having variable elasticity, the tubular form having a first multiplicity of knitted or interwoven lines, wherein each the line is knitted or interwoven with at least one non-conductive yarn; and a second multiplicity of conductive textile electrodes for sensing maternal and fetal electrical vital signals. The maternal and fetal electrical vital signals are selected from a group including maternal heart rate, fetal heart rate and electromyogram (EMG) activities including uterine activities.

Each conductive textile electrode includes a third multiplicity of vertically-aligned line segments, wherein each segment is formed within the knitted or interwoven lines with a non-conductive yarn and a conductive yarn. Each conductive textile electrode further includes a skin-side face configured to electrically conduct the signal from a predetermined external surface region of a pregnant woman. The predetermined external surface region is selected from a group including the abdomen, the perineum and buttocks of the pregnant woman.

Each conductive textile electrode is adapted to be in communication flow with a processor, adapted to process and analyze the electric signals acquired by the textile electrodes.

The second multiplicity of conductive textile electrodes includes a preconfigured number of measuring electrodes and a preconfigured number of reference electrodes. Each measuring electrode is paired with at least one reference electrode. Thereby, the number of differential measurements produced from a single measuring electrode may be more than one, i.e., the number of differential measurements produced is the number of reference electrodes that the particular measuring electrode is paired with, each pairing providing a different differential measurement.

Furthermore, each given conductive textile electrode, in a specific measurement instance, may be paired with a preconfigured number of other conductive textile electrodes, wherein in each pairing, the given conductive textile electrode may serve either as a measuring electrode or as a reference electrode, thereby facilitating substantial increase in the number of differential measurements acquired, in that specific measurement instance, beyond the second multiplicity of the conductive textile electrodes.

The measuring electrodes and the reference electrodes are positioned, within the maternal garment, in preconfigured locations. The position of the measuring electrodes and the reference electrodes are preconfigured to thereby optimize the spatial coverage of the uterine.

Preferably, the pairing of the measuring electrodes and respective reference electrodes is preset using the processor. The number of measuring electrodes, the number of reference electrodes and the pairing thereof are preset to thereby optimize the signal to noise (SNR) ratio.

The tubular form has a designated knitting or interweaving density, and wherein one or more designated regions have a knitting or interweaving density that is higher than the designated knitting or interweaving density of the tubular form, thereby providing the variable elasticity, to enable stable conductive contact of the skin-side face of each the electrode with the skin of the pregnant woman.

Preferably, the maternal and fetal monitoring is performed continuously, day and night, while performing everyday life chores.

Preferably, the processor is adapted to alert at least one preconfigured receiving entity, upon detecting a health hazard. The preconfigured receiving entity is selected from the group including a smart personal electronic device of the pregnant woman, a smart personnel electronic device of another person, a medical personal, and a remote center.

According to further teachings of the present invention, there is provided a method for maternal and fetal monitoring including the steps of:
  a) Wearing a knitted or interwoven smart maternal garment having a plurality of textile electrodes integrally knitted or interwoven therein, the textile electrodes being in communication flow with a processor.
  b) Acquiring electrical mixed common, maternal and fetal electrical vital signals from a plurality of external surface regions of a pregnant woman, respectively using a plurality of textile electrodes integrally knitted or interwoven into a maternal garment.
  c) Optimally-weighted summing-up the acquired mixed maternal and fetal electrical vital signals to thereby form a summed-up mixed signal, having a substantially higher SNR than either of the acquired maternal and fetal electrical vital signals.
  d) Analyzing the summed-up mixed signal to thereby extract a maternal signal from the summed-up mixed signal and maternal-related-parameters thereof
  e) Healing the summed-up mixed signal, including deleting the extracted maternal signal from the summed-up mixed signal, to thereby form a healed-summed-up mixed signal.
  f) Analyzing the healed-summed-up mixed signal to thereby extract a fetal signal from the healed-summed-up mixed signal and fetal-related-parameters thereof.

The maternal-related-parameters are selected from the group including heart rate, oxygen saturation, respiratory rate, blood pressure, skin temperature and ECG parameters such as ST elevation and depression.

The fetal-related-parameters are selected from the group including heart rate, spatial position of the heart inside the womb, body spatial orientation inside the womb, motion inside the womb and body dimensions.

According to further teachings of the present invention, there is provided a method for maternal and fetal monitoring including the steps of:
  a) Wearing a knitted or interwoven smart maternal garment having a plurality of textile electrodes integrally knitted or interwoven therein, the textile electrodes being in communication flow with a processor.
  b) Acquiring electrical mixed common, maternal and fetal electrical vital signals from a plurality of external surface regions of a pregnant woman, respectively using a plurality of textile electrodes integrally knitted or interwoven into a maternal garment.
  c) Optimally-weighted summing-up the acquired mixed maternal and fetal electrical vital signals to thereby form a summed-up maternal signal, having a substantially higher SNR than either of the acquired maternal and fetal electrical vital signals.
  d) Analyzing the summed-up maternal signal to thereby extract a maternal signal from the summed-up maternal signal.
  e) Healing the acquired mixed maternal and fetal electrical vital signals, including deleting the extracted maternal signal from the respective acquired mixed maternal and fetal electrical vital signal, to thereby form a plurality of healed-maternal ECG signals.
  f) Optimally-weighted summing-up the healed-maternal ECG signals to thereby form a summed-up coherent fetal signal, having a substantially higher SNR than either of the healed-maternal ECG signals.
  g) Analyzing the summed-up coherent fetal signal to thereby extract a fetal signal from the summed-up coherent fetal signal.

Optionally, the method further includes analyzing the summed-up coherent fetal signal to thereby extract the EMG signal formed by electromyogram (EMG) activities including uterine activities, from the summed-up coherent fetal signal.

The extracting and analyzing of the maternal signal from the summed-up maternal signal includes:
  a) Detecting the peaks in the maternal QRS complexes using the summed-up maternal signal, the maternal QRS complexes peaks being substantially stronger than the fetal QRS complexes.
  b) Determining the boundary of each detected maternal QRS complex.
  c) Analyzing the summed-up maternal signal to thereby extract the maternal signal and determine the maternal HR.
  d) Analyzing each detected maternal QRS complex to thereby detect health hazardous data.

The extracting and analyzing of the fetal signal from the summed-up coherent fetal signal includes:
  a) Detecting the peaks of the maternal QRS complexes in the summed-up maternal signal, the maternal QRS complexes peaks being substantially stronger than the fetal QRS complexes.
  b) Determining the boundary of each detected maternal QRS complex.
  c) Deleting each detected maternal QRS complex from the respective acquired mixed maternal and fetal electrical vital signal and filling the gap, thereby forming a respective healed-maternal ECG signal.
  d) Optimally-weighted summing-up the healed-maternal ECG signals to thereby form a summed-up coherent fetal signal, having a substantially higher SNR than either of the healed-maternal ECG signals.
  e) Detecting the peaks of fetal QRS complexes in the summed-up coherent fetal signal.
  f) Determining the boundary of each detected fetal QRS complex.
  g) Analyzing the summed-up coherent fetal signal to thereby determine the fetal HR.
  h) Analyzing each detected fetal QRS complex to thereby detect health hazardous data.

The extracting and analyzing of the EMG signal from the summed-up coherent fetal signal includes:
  a) Detecting the peaks in the maternal QRS complexes in the summed-up maternal signal;
  b) Determining the boundary of each detected maternal QRS complex.
  c) Deleting each detected maternal QRS complex from the respective acquired mixed maternal and fetal electrical vital signal and filling the gap, thereby forming a respective healed-maternal ECG signal.
  d) Detecting the peaks of the fetal QRS complexes in the summed-up coherent fetal signal.

e) Determining the boundary of each detected fetal QRS complex.

f) Deleting each detected fetal QRS complex from the summed-up coherent fetal signal and filling the gap, thereby forming an EMG summed-up signal.

g) Analyzing the EMG summed-up signal.

The method of filling the gap includes, for example, by linear interpolation or spline.

The summed-up coherent fetal signal may contain more than one fetus and wherein the fetal QRS complexes of the signal of each fetus is separated based on different heart rate and/or different phase normal or inverted QRS Complex. The separation of the signal of each fetus may be performed using Fourier transform.

It should be noted that the maternal garment is worn without attaching either of the electrodes, regardless of the precise bodily positioning of each electrode, regardless of the chronological stage of the pregnancy, and regardless of the amount of stretching of the tubular form and of each electrode.

BRIEF DESCRIPTION OF THE DRAWINGS

The present invention will become fully understood from the detailed description given herein below and the accompanying drawings, which are given by way of illustration and example only and thus not limitative of the present invention:

FIG. 2a is a side view illustration of the underpants shown in FIG. 1, worn by a monitored pregnant woman.

FIG. 2b is a front view of the underwear monitoring-garment, as shown in FIG. 2a.

FIG. 2c is a back view of the underwear monitoring-garment, as shown in FIG. 2a.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided, so that this disclosure will be thorough and complete, and will fully convey the scope of the invention to those skilled in the art.

An embodiment is an example or implementation of the inventions. The various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "one embodiment", "an embodiment", "some embodiments" or "other embodiments" means that a particular feature, structure, or characteristic described in connection with the embodiments is included in at least one embodiments, but not necessarily all embodiments, of the inventions. It is understood that the phraseology and terminology employed herein is not to be construed as limiting and are for descriptive purpose only.

Methods of the present invention may be implemented by performing or completing manually, automatically, or a combination thereof, selected steps or tasks. Meanings of technical and scientific terms used herein are to be commonly understood as to which the invention belongs, unless otherwise defined. The present invention can be implemented in the testing or practice with methods and materials equivalent or similar to those described herein.

It should be noted that the present invention will often be described in terms of the monitoring-garment being an underpants, but the present invention is not limited to an underpants being the monitoring-garment, and other types of garment, at least partially worn adjacently to the body of the monitored pregnant woman can be used as a monitoring-garment.

It should be noted that the present invention will be described in terms of the optional mobile device being a smart-phone, but the mobile device of present invention is not limited to being a smart-phone, and includes all types of mobile devices having a central processing unit and memory, including a mobile phone, laptop, a PDA, a processing pad, etc., all having Bluetooth or any other wireless communication capabilities. According to the teachings of the present invention, there is provided an independent, seamless and preferably substantially continuous health monitoring system, designed for use by a healthy living being but also suitable for non-healthy living being.

Figure 1:
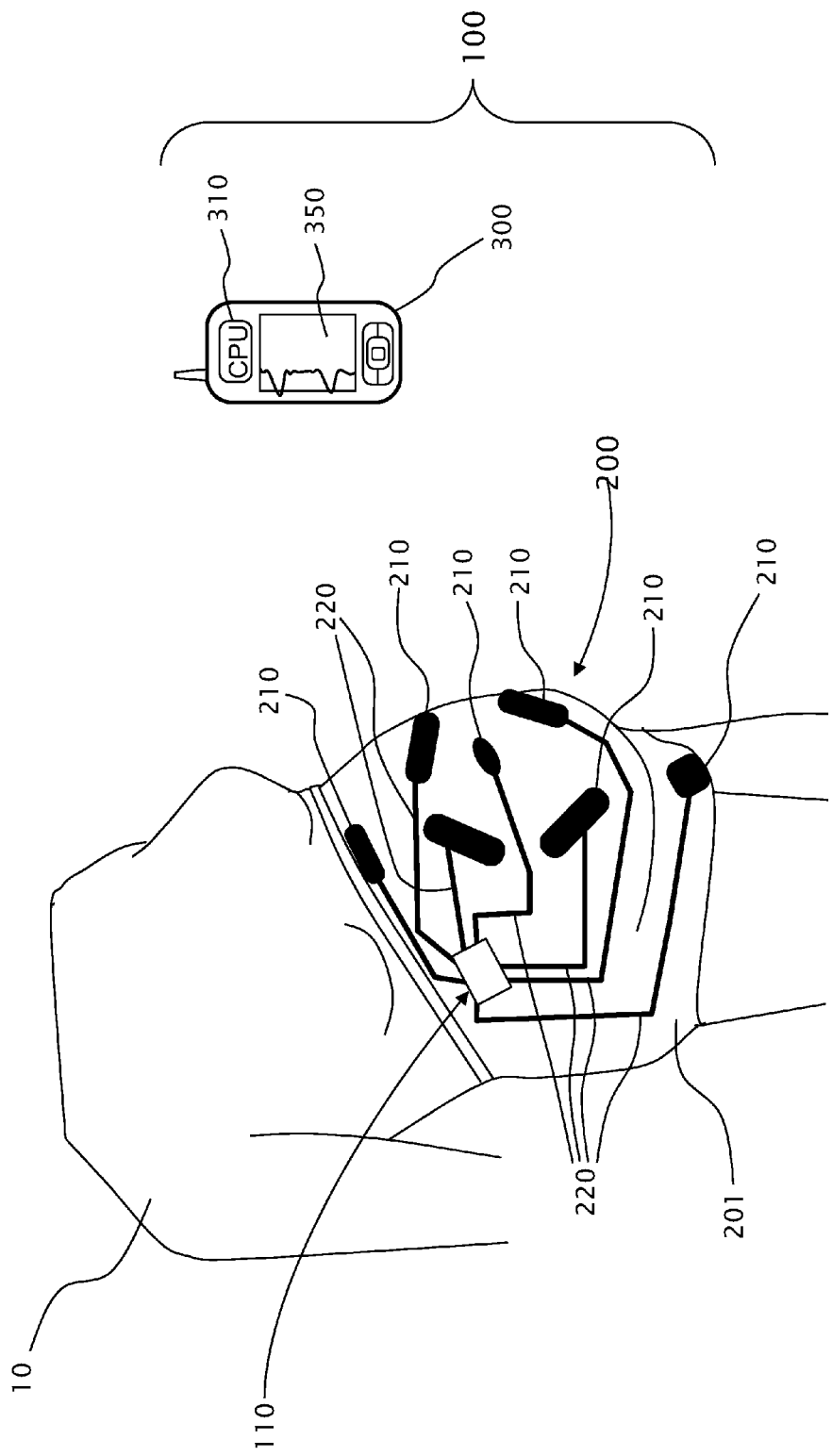
FIG. 1 schematically illustrates a smart maternal monitoring garment for maternal and fetal monitoring, being an exemplary underwear monitoring-garment, according to embodiments of the present invention.

Reference now made to the drawings. FIG. 1 illustrates a seamless wearable fetal monitoring system 100 including a smart garment 200 worn by a monitored pregnant woman 10, according to embodiments of the present invention, smart garment 200 being an exemplary underwear monitoring-garment. Fetal monitoring system 100 further includes a garment-control device 110 and preferably, a receiving device such as a mobile device 300, having a remote-processor 310, according to embodiments of the present invention.

FIG. 2a is a side view illustration of smart garment 200, worn by a monitored pregnant woman 10, smart garment 200 being an exemplary leotard. FIG. 2b is a front view illustration of smart leotard 200 and FIG. 2c is a back view illustration of smart leotard 200, as shown in FIG. 2a.

Smart garment 200 is a non-limiting, exemplary monitoring-garment item, wherein smart garment 200 is, preferably, a knitted garment and wherein one or more textile electrodes 210 are knitted there within, when smart garment 200 is fabricated. The textile electrodes 210 are made of conductive yarn, wherein electrocardiogram (ECG) signals, being detected by textile electrodes 210. The signals are then transferred via knitted conductive traces along the knitted fabric to an innovative device, which analyzes the data in real-time.

In some embodiments textile electrodes 210 are interwoven and in some embodiments smart garment 200 is interwoven. Textile electrodes 210 and smart garment 200 will be described herein, with no limitations, as being knitted, but textile electrodes 210 and garment 200 may also be interwoven, within the scope of the present invention.

Typically, textile electrodes 210 are integrated in various positions within smart garment 200, in order to cope with the changing of position and the growing of the fetus inside the mother's womb. Textile electrodes 210 acquire mixed electrical maternal and fetal vital signals, and possibly EMG signals. Garment-control device 110 reads the mixed signals from the various textile electrodes 210 and in some embodiments, garment-control device 110 selects a signal determined to be the "best signal", according to preconfigured criteria. For example, signals that best match a master expected signal ("gold-standard" fetal data).

However, preferably, garment-control device 110 reads the mixed signals from a multiplicity of textile electrodes 210, makes (optionally) an initial sorting of the multiplicity of signals, and optimally performs a weighted summing-up of the acquired mixed electrical maternal and fetal vital signals, to thereby form a summed-up electrical signal having a substantially higher SNR than either of the acquired mixed electrical maternal and fetal electrical vital signals.

Typically, textile electrodes 210 are surface-to-surface contact textile sensors, used for measuring maternal and fetal electrical vital signals such as ECG signals and other vital signals, such as cardiotocography signals and other medical measurements on the skin, without any skin preparation such as needed with current wet electrode (usually gel) as well as on hairy skin (currently, usually being shaved).

The multiplicity of textile electrodes 210 may include a preconfigured number of measuring electrodes 212 and reference electrodes 214 that may be selectively paired, for example using garment-control device 110, to form ECG leads. Each measuring electrodes 212 is paired with at least one reference electrode 214, facilitating acquiring more ECG differential measurements than the number of textile electrodes 210 that serve as measuring electrodes 212. The number textile electrodes 210 that serve as measuring electrodes 212 may be controlled, for example using garment-control device 110. Hence, which textile electrode 210 serves as measuring electrode 212 and with which one or more reference electrode 214 that measuring electrode 212 is paired, can be pre-programed and re-programed. Using this unique capability, seamless wearable fetal monitoring system 100 may be suited, for example, to the advancement of the pregnancy and abdomen dimensions, or for any other reason.

It should be noted that the annotation of measuring electrodes 212 and reference electrodes 214 in the Figures are shown by way of example only, with no limitations. Textile electrodes 210 may be placed at predetermined external surface regions selected from a group including the abdomen, the perineum and buttocks of the pregnant woman.

Each textile electrode 210 is operatively connected to a preferably detachable garment-control device 110, by a conductive trace 220 conductive stripes or any other electric wiring. Optionally, conductive traces 220 are also knitted into smart garment 200, when smart garment 200 is fabricated. Alternatively, conductive traces 220 are attached to smart garment 200.

Figure 4:
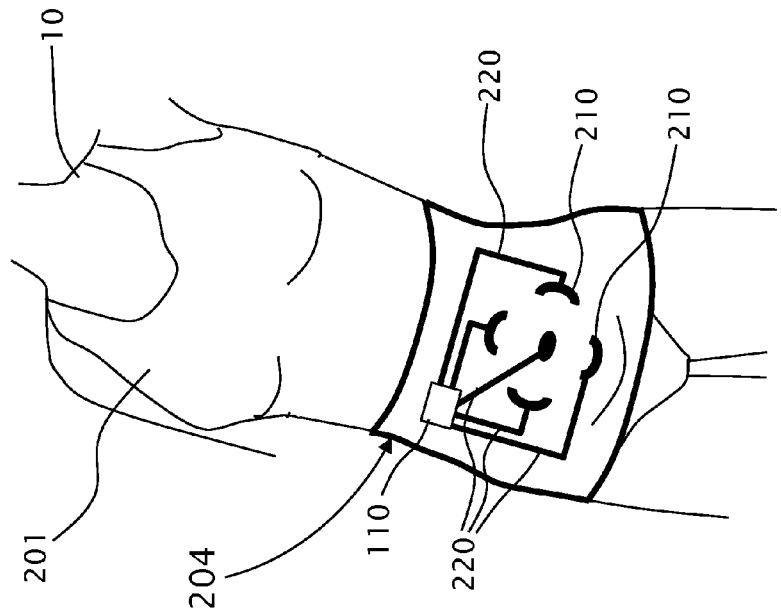
FIG. 4 is a front perspective view illustration of the system shown in FIG. 1, integrated into a plain tubular garment, wrapped around the abdominal region of a monitored pregnant woman.
Figure 3:
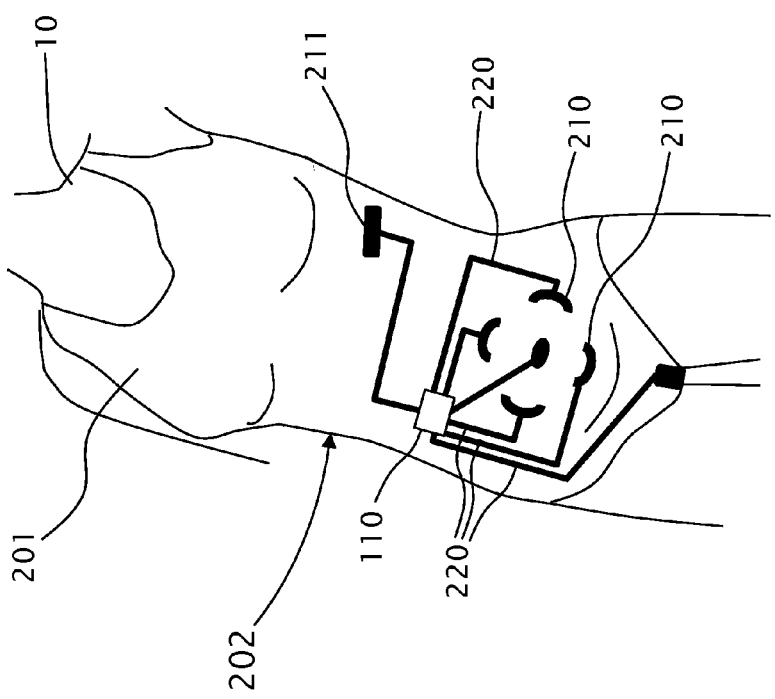
FIG. 3 is a front perspective view illustration of the system shown in FIG. 1, integrated into a leotard-type garment, worn by a monitored pregnant woman.

Typically, smart garment 200 looks like regular underpants and preferably, the textile electrode 210 are embedded therein. A pregnant woman 10 can easily wear the underpants in any situation where he or she is used to. However, smart garment 200 may be replaced by a leotard-type smart garment 202, as shown in FIG. 3, or a tubular smart garment 204, as shown in FIG. 4, or other forms. In the example shown, leotard-type smart garment 202 includes a textile electrode 211 that is positioned proximal to the mother's heart, to thereby obtain a good maternal ECG signal. After wearing the smart garment, no attaching of electrodes or placement adjustments are required from the user. Simply wear the smart garment and activate the system.

Figure 5:
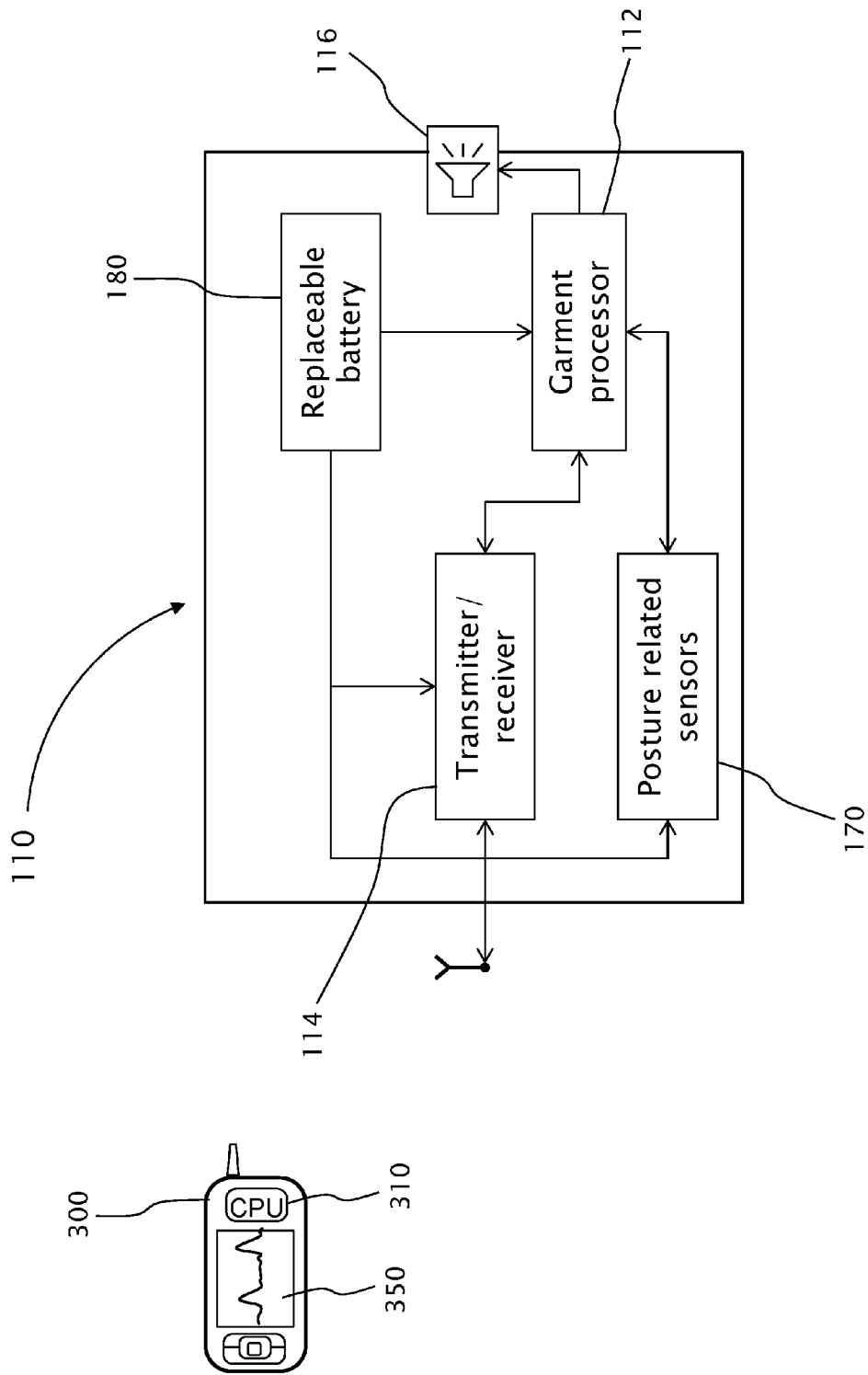
FIG. 5 is a schematic block diagram of one embodiment of the garment-control device shown in FIGS. 1, 2a and 2b.

Reference is also made to FIG. 5, a schematic block diagram of one embodiment of garment-control device 110. Garment-control device 110 is also mounted onto garment-body 201 of a smart garment 200 is garment-control device 110, wherein traces 220 interconnect all of the sensors (210, 212 and 214) with garment-control device 110, optionally by traces 220 knitted into monitoring-garment 200. Garment-control device 110 includes a garment-processor 112 and a preferably replaceable and/or rechargeable battery 180, wherein garment-control device 110 and battery 180 are preferably removable, to allow machine washing of the smart garment. Rechargeable battery 180 may be part of garment-control device 110 of separated from garment-control device 110. Preferably, garment-control device 110 further includes a transmitter 114, typically short range transmitter such as Bluetooth or Wi-Fi, facilitating wireless communication between garment-processor 112 and remote-processor 310 of a mobile device 300. Optionally, garment-control device 110 further includes an alerting unit 116.

In one embodiment of the present invention, garment-control device 110 transmits the sensed data, as provided by the sensors (210, 211 and 212), to remote-processor 310 of mobile device 300, via transmitter 114. In other embodiments of the present invention, garment-processor 112 analyzes the sensed data obtained by one or more of the sensors (210, 211 and 212) and prevents sensed data that is well within a preconfigured range of normal parameter, from being transmitted by transmitter 114 to remote-processor 310. Thereby, substantially reducing the transmittal time and saving in transmittal power.

Optionally, embedded garment-processor 112 has a filtering function to substantially limit the transmissions to the mobile device. One part of that function is limiting the transmission, when there are no problems detected and selecting only the suspected abnormal data to be transmitted. This function significantly reduces the amount of energy needed, thus preserving the battery power. In addition, the algorithms determine the sensing rate: while in normal state the rate may be low, when sensed data is closer to abnormality values, the sensing and transmission rates are higher.

In some preferred embodiments of the present invention, garment-processor 112 analyzes the sensed data obtained by one or more of the sensors (210, 211 and 212) to thereby determine if a health hazardous situation has occurred. In such an event, garment-processor 112 activates an alerting unit 116, coupled to operate with garment-processor 112, to thereby provide a personal-alert to person 10 or any other predetermined receiving unit, including receiving unit of medical care personal. The personal-alert may be in the form of an audio sound, a light indication, any other form known in the art, or a combination thereof.

Optionally, garment-control device 110 is operatively anchored in a corresponding docking station that is attached to monitoring-garment 100, and operatively attached to traces 220.

As indicated hereinabove, fetal monitoring system 100 of the present invention preferably includes a mobile device 300, having a remote-processor 310. Remote-processor 310 receives sensed data from monitoring-garment 100, preferably, at least partially processed, and may further analyze the received data, as needed, and determines if a health hazardous situation, that justifies the issuing of a personal-alert has occurred. In such an event, remote-processor 310 activates an alarm indicator 116, coupled to operate with remote-processor 310, to thereby alarm person 10 with a personal-alert 350. The personal alert may be in the form of an audio sound, at least one image frames, a video, an SMS, or any other form known in the art, or a combination thereof.

In variations of the present invention, the definition of the abnormality of the physiological or chemical parameter is personally adaptive, wherein the "normal" health state of a particular monitored living being is personally set. In variations of the present invention, the definition of the abnormality is dynamically adaptable per the changing state over time of the living being.

Upon detecting abnormal health related parameters, or an abnormal state determined as a result from an analysis of combined inputs acquired from different sensors, or from a trends analysis, remote-processor 310 sends a personal-alert through smart-phone 300. Optionally or additionally, remote-processor 310 sends personal-alert information to a predetermined external recipient. Optionally, remote-processor 310 analyzes and determines the correlation between the detected parameters of two or more of the detected, thereby creating correlated parameters. When the detected correlated parameters are determined to be abnormal, the alerting unit is operatively activated to alert one or more predetermined alert receiving entities.

It should be further noted that some of the processing tasks may be performed at a remote monitoring center. The garment-processor 112 or mobile device 300 may send the data (sensed data or at least partially analyzed sensed data) to any remote processor, which can further process the information, compare the obtained data to corresponding data obtained from other monitored people, make statistics-based decisions and other decision-making issues to improve alerts sensitivity and specificity (for example by detecting suspicious trends that did not trigger the automatic alert but a physician may want to further check the person) and providing information for assisting the treatment of the living being once getting to a treating facility.

Preferably, the health monitoring and self-alert system includes sensors for detecting the characteristics of the physical activities and posture of the living being, for example, acceleration sensors 170 (see FIG. 5), pressure sensors, orientation sensors, etc. Acceleration sensors 170 may be integrated within garment processor 110, and/or at other preconfigured locations in garment-body 201.

Figure 6:
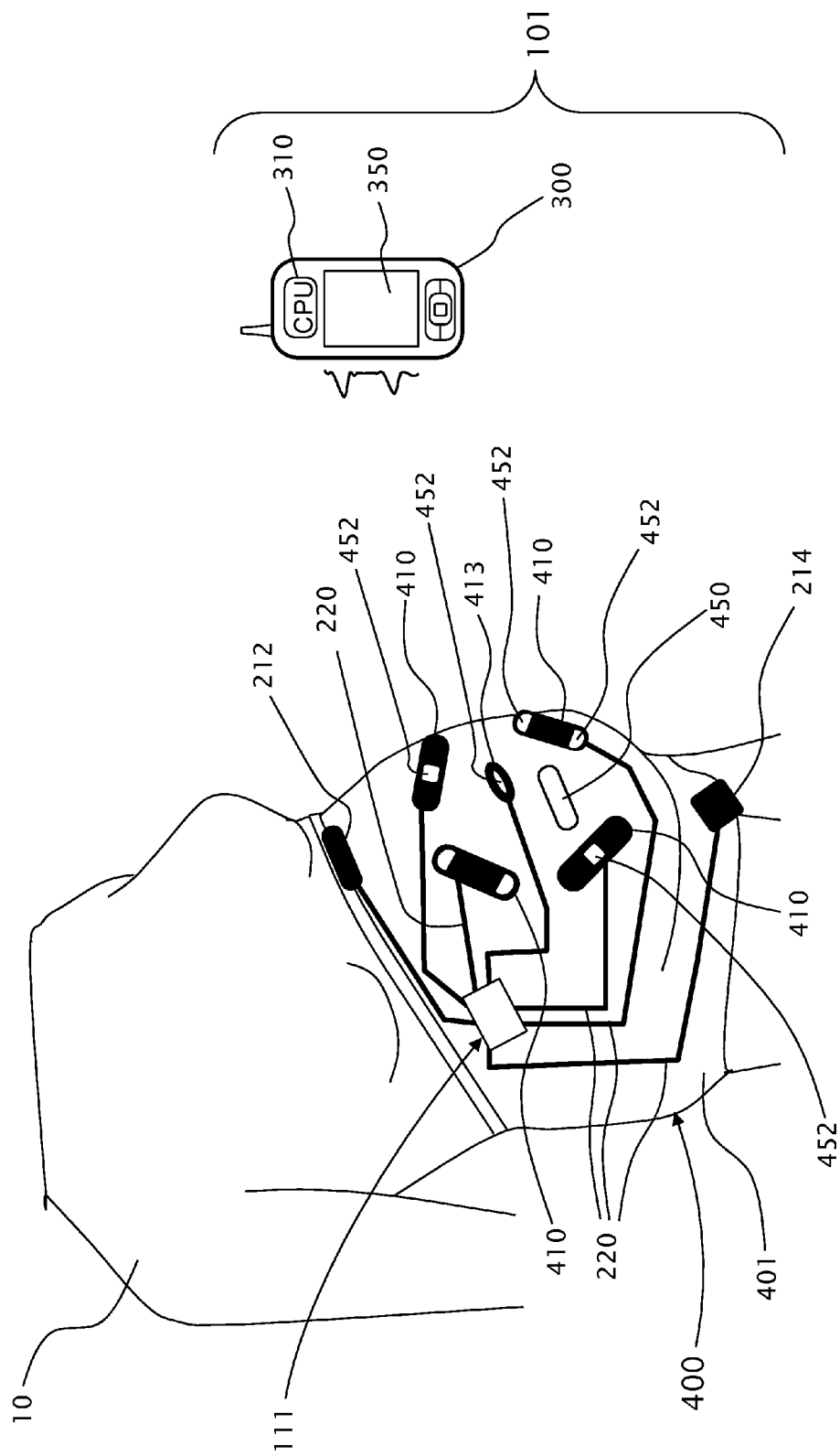
FIG. 6 schematically illustrates a seamless wearable fetal monitoring system including a smart leotard, being an exemplary underwear monitoring-garment, according to other embodiments of the present invention.

FIG. 6 schematically illustrates a seamless wearable fetal monitoring system 101 including a smart garment 400, being an exemplary underwear monitoring-garment, according to other embodiments of the present invention. Smart fetal monitoring system 101 is similar to smart fetal monitoring system 100, but further includes at least one textile pressure sensor 450 for detecting activity of the uterus, such as contractions. Textile pressure sensor 450 may be embodied as separate detectors and/or embodied within ECG electrode (or other textile sensors) 210 to form a multi-purpose sensor 410. The textile pressure sensor may be embodied as a combination of more than one sensing element 452, within ECG electrode (or other textile sensors) 210.

In variations of the present invention, motion of the fetus within the mother's uterus, is detected, using multiple ECG electrodes. The SNR ration of each ECG electrode is measure whereas it is assumed that the heart of the fetus is spatially positioned closest to the electrode having the best SNR. As the fetus moves, the spatially position of the heart of the fetus is moving to be closer to a different ECG electrode. Since to position of each ECG electrode with respect to the mother's uterus is substantially fixed and known, these changes in the SNR of the ECG electrodes can be analyze to proximate the spatial position of the heart of the fetus as well as the position and posture-orientation of the fetus itself.

It is an aspect of the present invention to provide methods for maternal and fetal monitoring, using seamless wearable fetal monitoring system 100 and variations thereof. The method assumes M textile electrodes 210, some of which M textile electrodes 210 are preset to serve as reference electrodes 214 and the rest, N textile electrodes 210, are preset to serve as measuring electrodes 212, wherein the presetting is performed using garment-control device 110.

To start using seamless wearable fetal monitoring system 100 a pregnant woman 10 wears a knitted or interwoven smart maternal garment 200, having of textile electrodes 210 integrally knitted or interwoven therein, the textile electrodes 210 being in communication flow with garment-control device 110, and activates fetal monitoring system 100. Garment-control device 110 starts acquiring electrical mixed common, maternal and fetal electrical vital signals from a predetermined external surface region of a pregnant woman, using a plurality of textile electrodes integrally knitted or interwoven into a maternal garment. The monitoring may be performed continuously, 24/7.

It should be noted that smart maternal garment 200 is worn without attaching either of the textile electrodes 210, regardless of the precise bodily positioning of each textile electrode 210, regardless of the chronological stage of the pregnancy, and regardless of the amount of stretching of the textile tubular form and of each textile electrode 210.

Figure 7A:
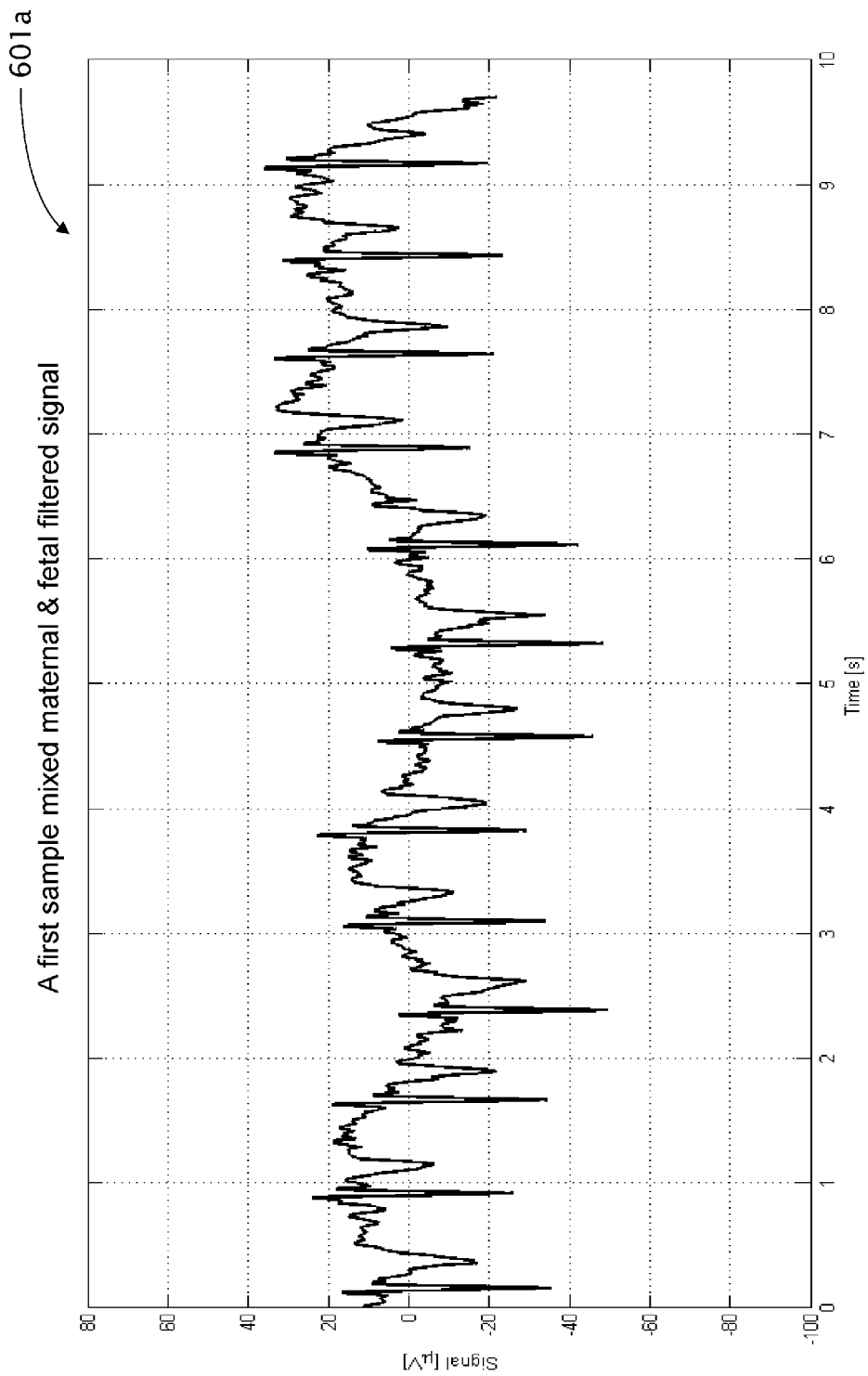
FIGS. 7a-7d show examples of 4 mixed maternal and fetal electrical signals, each provided by a respective measuring textile electrode.
Figure 7B:
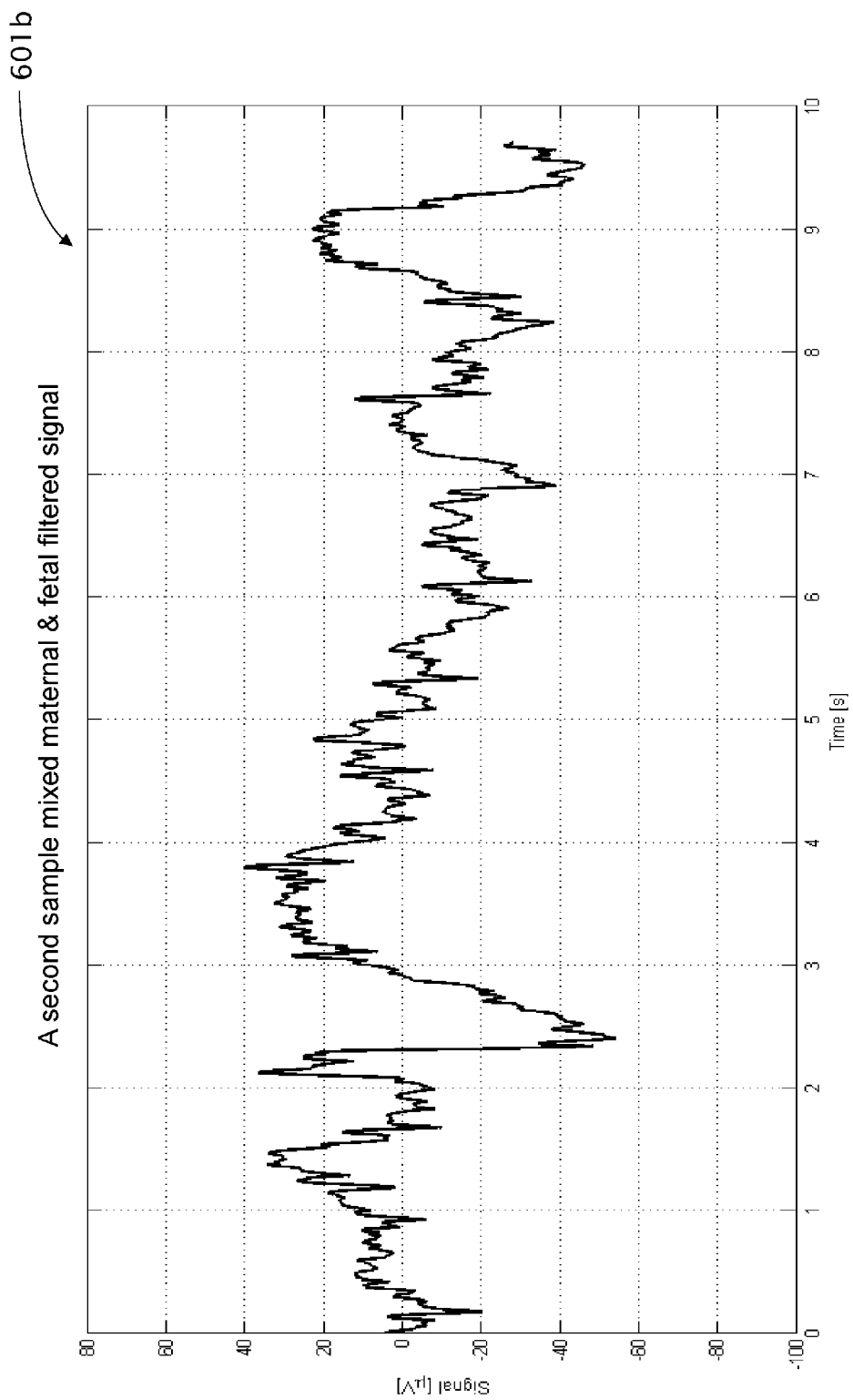
Figure 7C:
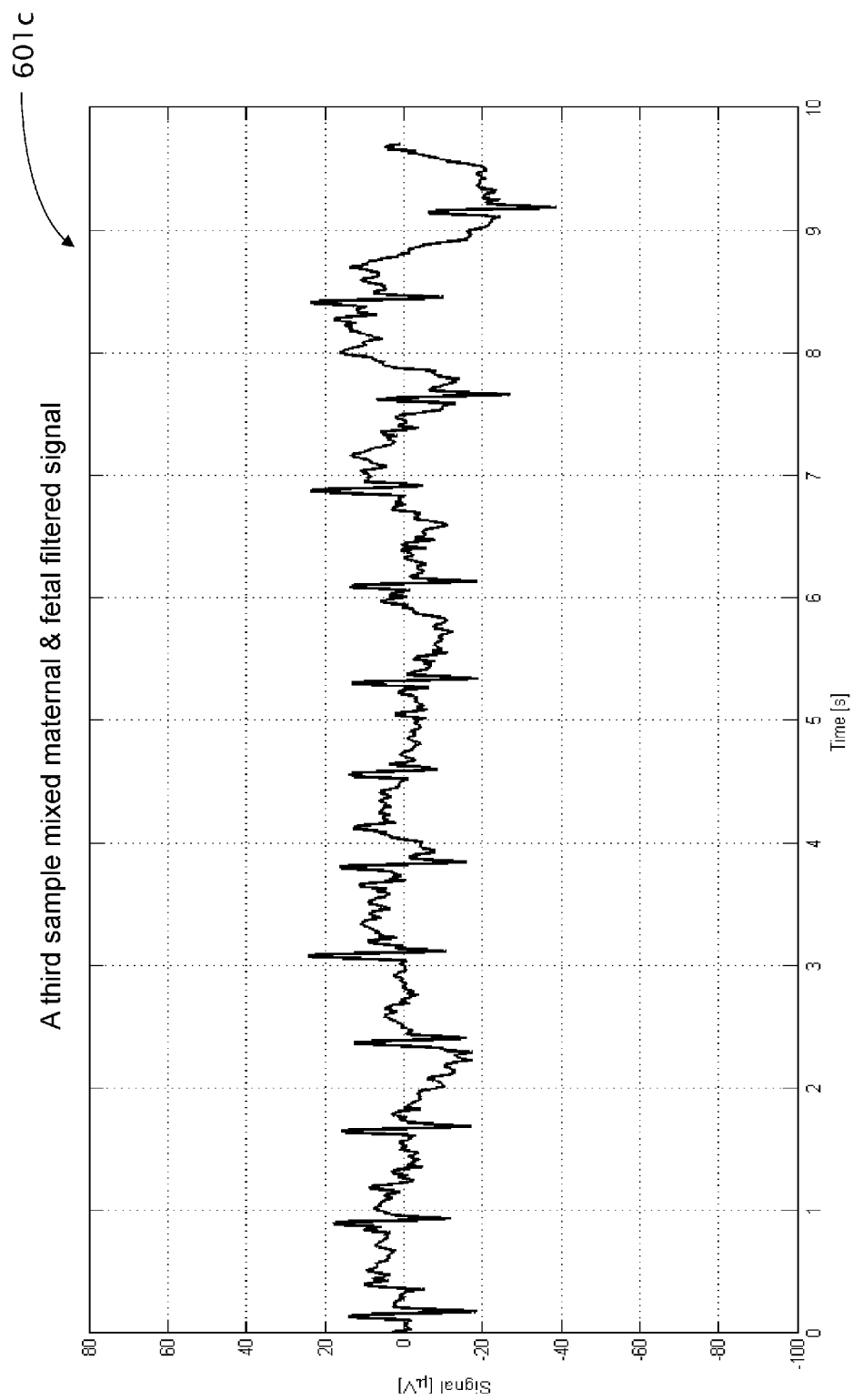
Figure 7D:
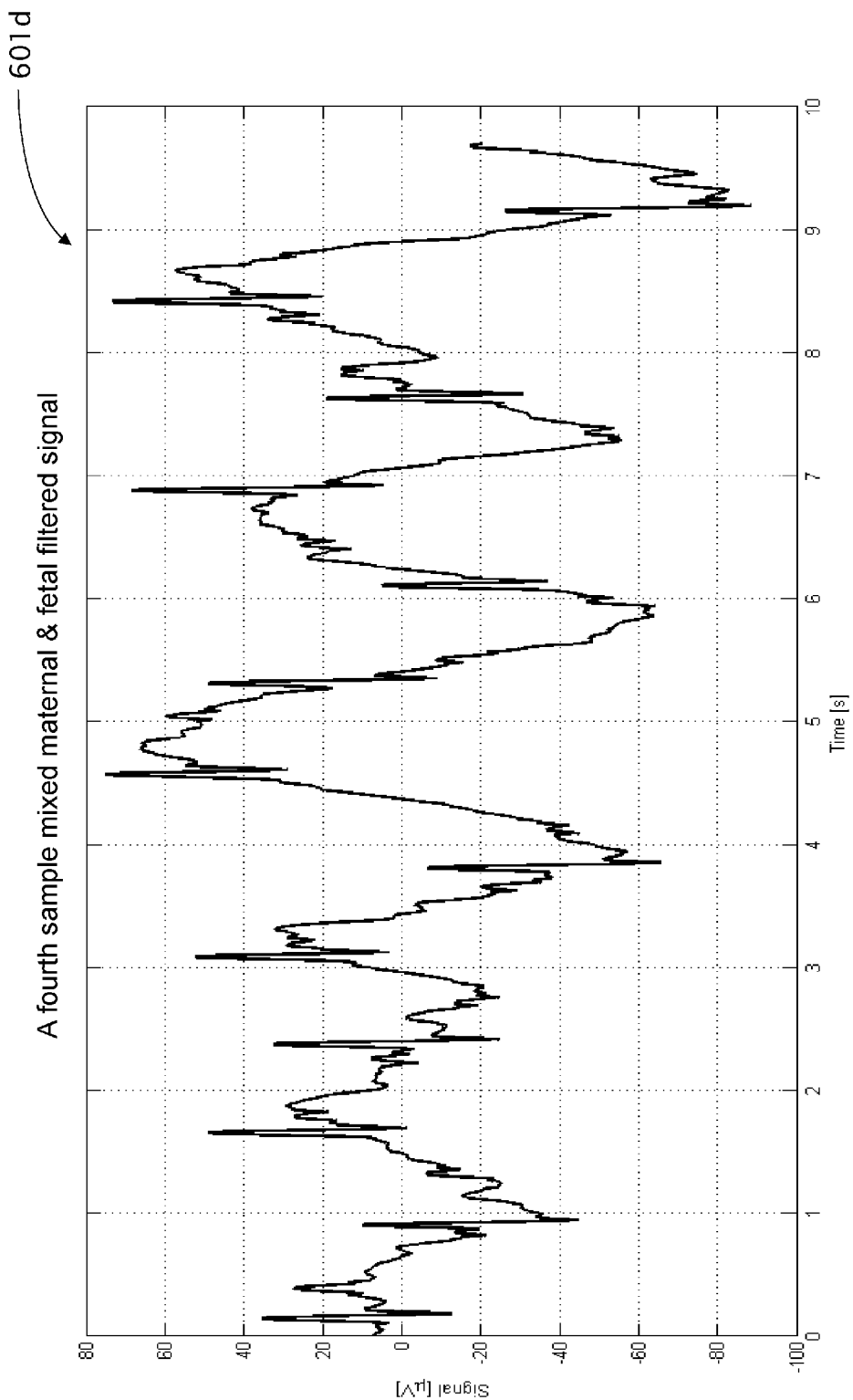
Figure 7E:
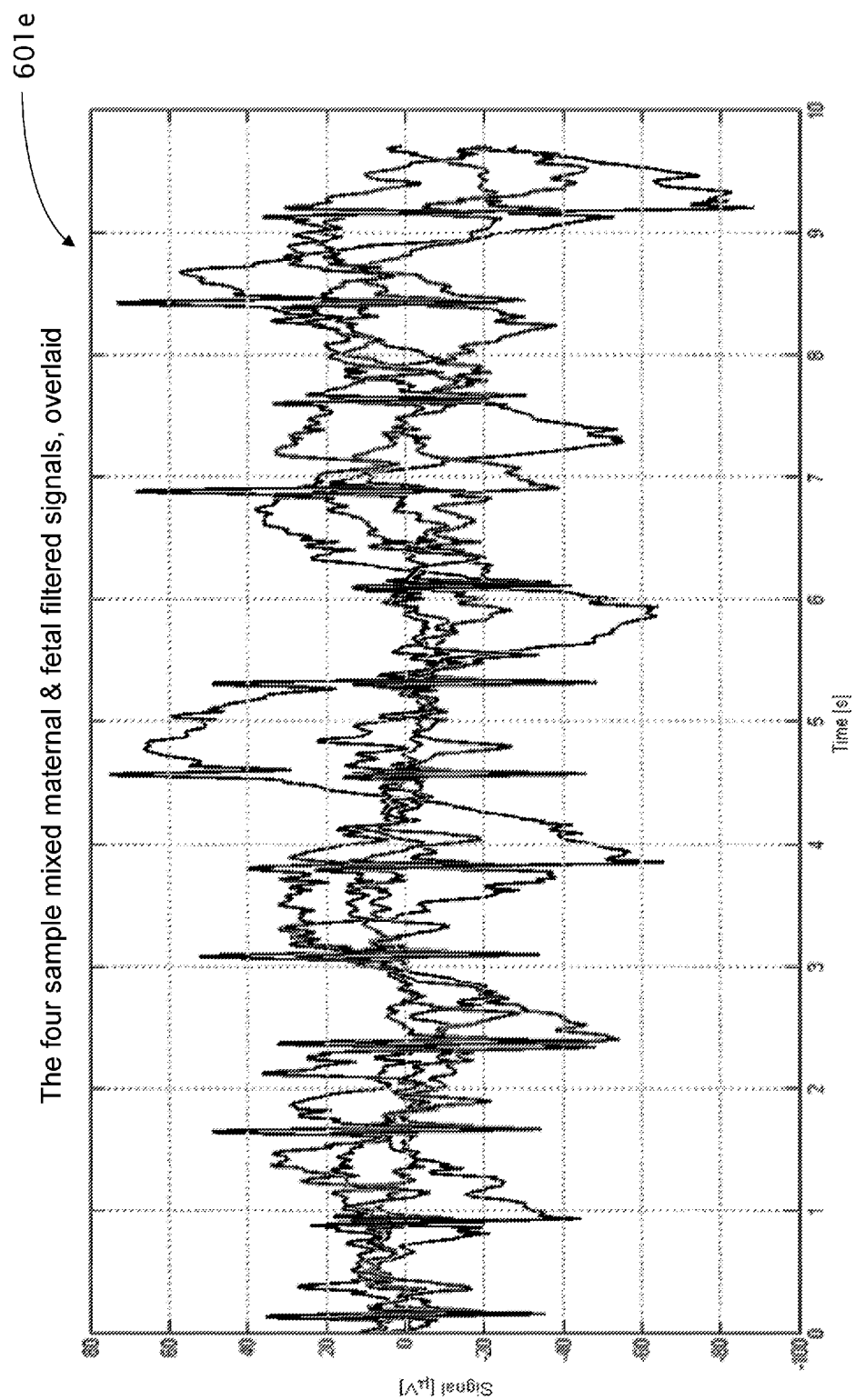
FIG. 7e shows the 4 mixed maternal and fetal electrical signals illustrated in FIGS. 7a-7d, overlaid on a mutual time axis, as provided simultaneously by respective four measuring textile electrodes.

Reference is now made to FIGS. 7a-7e. FIG. 7a shows a graph 601a of an example of a first mixed maternal and fetal electrical signal, as provided simultaneously by a respective measuring textile electrode 212. FIG. 7b shows a graph 601b of an example of a second mixed maternal and fetal electrical signal, as provided simultaneously by a respective measuring textile electrode 212. FIG. 7c shows a graph 601c of an example of a third mixed maternal and fetal electrical signal, as provided simultaneously by a respective measuring textile electrode 212. FIG. 7d shows a graph 601d of an example of a fourth mixed maternal and fetal electrical signal, as provided simultaneously by a respective measuring textile electrode 212. FIG. 7e shows a graph 601e of the 4 mixed maternal and fetal electrical signals illustrated in FIGS. 7a-7d, overlaid on a mutual time axis, as provided simultaneously by the respective four measuring textile electrodes. The four raw signals have different amplitudes, and different phases. Empirically, with no limitations, the following observations are made:

The maternal and fetal signals are not correlated. Although normally, their HR's are different, their ranges may be partially overlapping.

The maternal and fetal ECG signal may ride on slow (<0.5 Hz) but very strong signals produced, for example, by muscles contraction, this low frequency signal interferes with reliable detection of the QRS complexes peaks. To substantially improve the signal flatness, polynomial filtering may be used, typically along with a derivative evaluation, wherein each raw signal is approximated by a polynomial and its derivative can be evaluated analytically. In some embodiments the polynomial filtering method combines Savitzky-Golay filtering and smoothing spline.

Typically, with no limitations, over 10 measuring textile electrodes 212 are used to improve SNR, wherein at least 2 measuring textile electrodes 212 are disposed proximal to the heart of the fetus.

Figure 8:
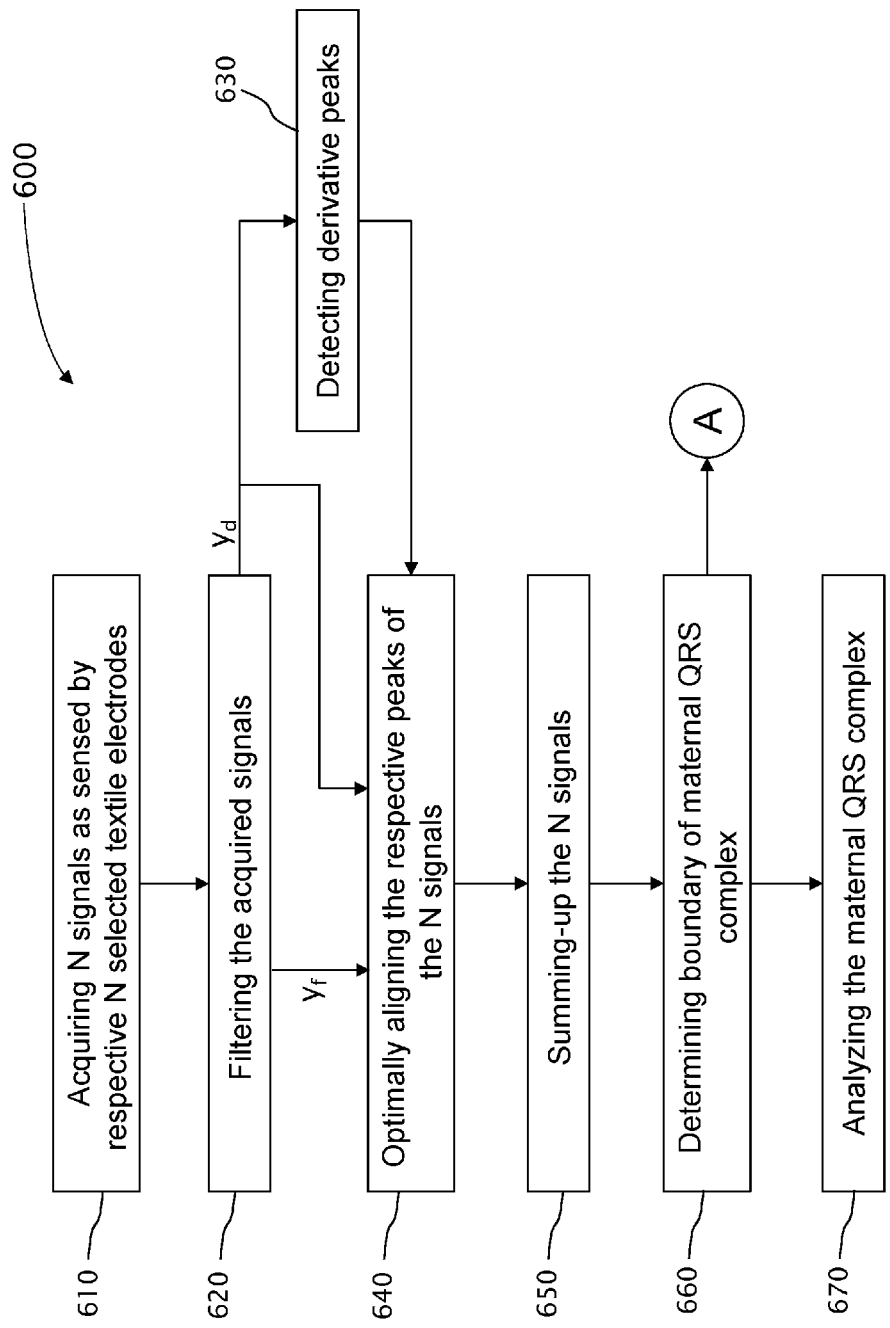
FIG. 8 is a schematic flowchart diagram outlining an example method for detecting, separating and analyzing a maternal QRS signal.

Reference is now made to FIG. 8, a schematic flowchart diagram 600 outlining an example method for detecting, separating and analyzing a maternal QRS signal from a multiplicity of simultaneously sensed mixed ECG signals. The maternal QRS complexes being substantially stronger than the fetal QRS complexes, the maternal QRS complexes are detected firstly.

Method 600 includes the following steps:

Step 610: acquiring N signals as sensed by respective N selected measuring textile electrodes 212.

Each measuring textile electrodes 212 senses a mixed ECG raw signal. A mixed ECG raw signal includes a maternal ECG signal, a fetal ECG signal, signals of electromyogram (EMG) activities including uterine activities, and other signals that at least a portion of them are referred to as noise.

Step 620: filtering the acquired signals.

Each sensed mixed ECG raw signal is preferably filtered to substantially reduce the noise. To substantially improve the signal flatness, polynomial filtering may be used, wherein each raw signal is approximated by a polynomial and its derivative can be evaluated analytically. In some embodiments the polynomial filtering method combines Savitzky-Golay filtering and smoothing spline. Typically, with no limitations, the filtering of each sensed mixed ECG raw signal yields to signals: $y_d$, a derivative signal that contains the QRS complexes peaks data; and $y_f$, representing the filtered signal.

Step 630: detecting derivative peaks.

Using the derivative signal $y_d$, garment-control device 110 detects derivative peaks that correspond to the maternal QRS complexes peaks of the respective sensed mixed ECG raw signal.

Step 640: Optimally aligning the respective peaks of the N signals.

Garment-control device 110 reads all the filtered mixed signals and respective derivative signals, makes (optionally) an initial sorting of the multiplicity of signals, and optimally calculates the best maternal QRS peaks alignment of the mixed ECG raw signals. Thereby, the phase shift of each mixed ECG raw signal is obtained.

To improve phase alignment process an analytical (complex) signal, such as Hilbert transform, may be used.

Step 650: summing-up the N signals.

Garment-control device 110 performs a weighted summing-up of the filtered mixed signals, after shifting each filtered mixed signal by the respective calculated phase shift, thereby forming a summed-up coherent maternal signal having a substantially higher SNR than either of the acquired mixed electrical maternal and fetal vital signals.

Step 660: determining the boundary of maternal QRS complexes.

Normally, each QRS complex starts from a first minimum point, reaches maximum and ends at a second minimum point. The first and second minimum points of each QRS complex are determined by garment-control device 110.

Step 670: analyzing the maternal QRS complexes.

Garment-control device 110 analyzes, for example by performing a morphologically analysis, and to determine the maternal HR and possibly detect health hazardous data.

{end of steps details of process 600}

Example

In the example shown in FIG. 7e, a graph 601e of 4 overlaid mixed maternal and fetal example signals, as provided simultaneously by respective four measuring textile electrodes 212, were shown.

Figure 9:
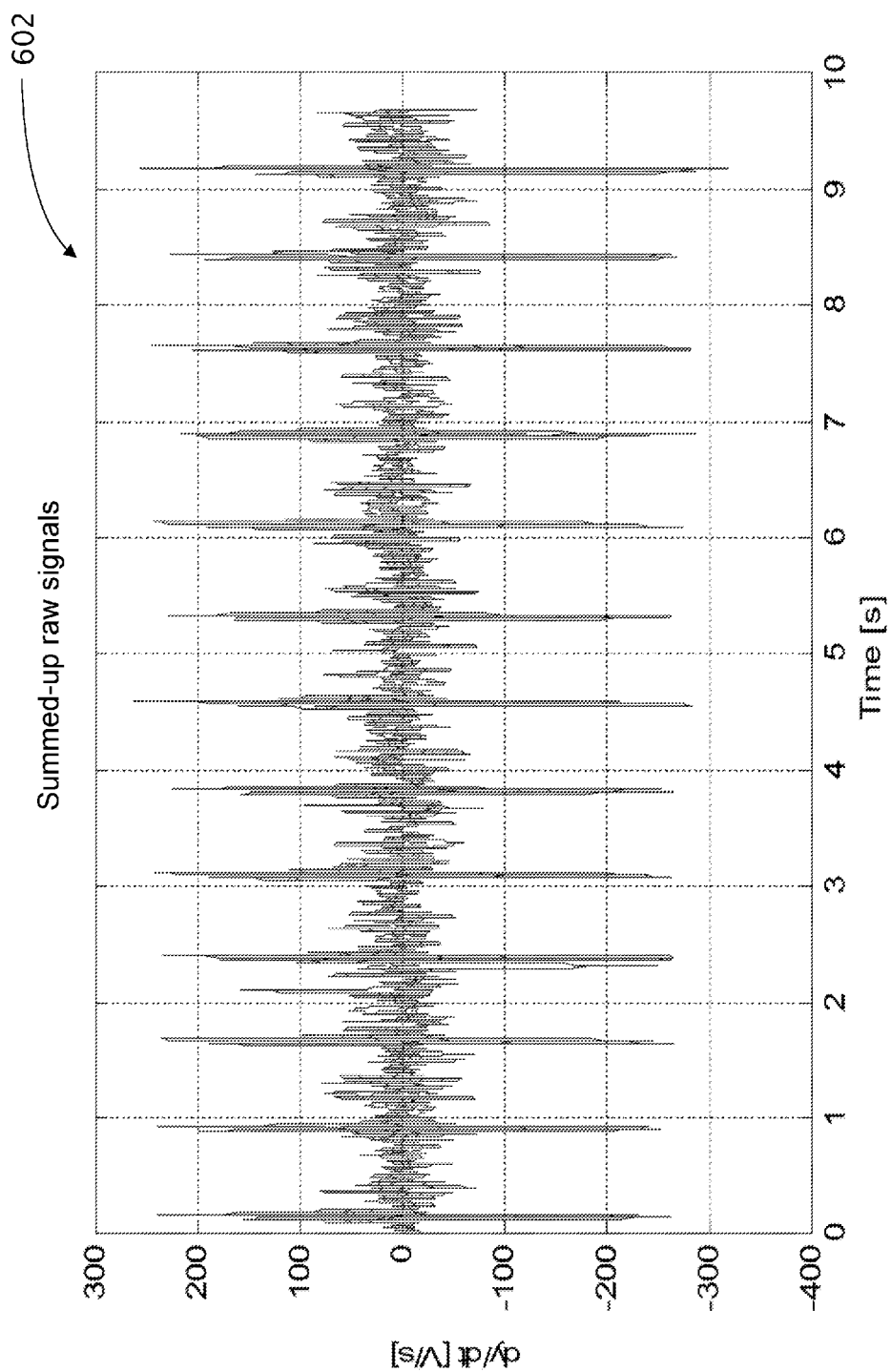
FIG. 9 shows the flattened, summed-up mixed maternal and fetal electrical signal, after optimally weighted summing-up the four signals shown in FIGS. 7a-7d.

Reference is also made to FIG. 9, showing the flattened, summed-up mixed maternal and fetal electrical signal, after the summing-up process (step 650) the four signals. The summed-up maternal signal is coherent, with good SNR and the maternal QRS complexes can be easily observed.

Figure 10:
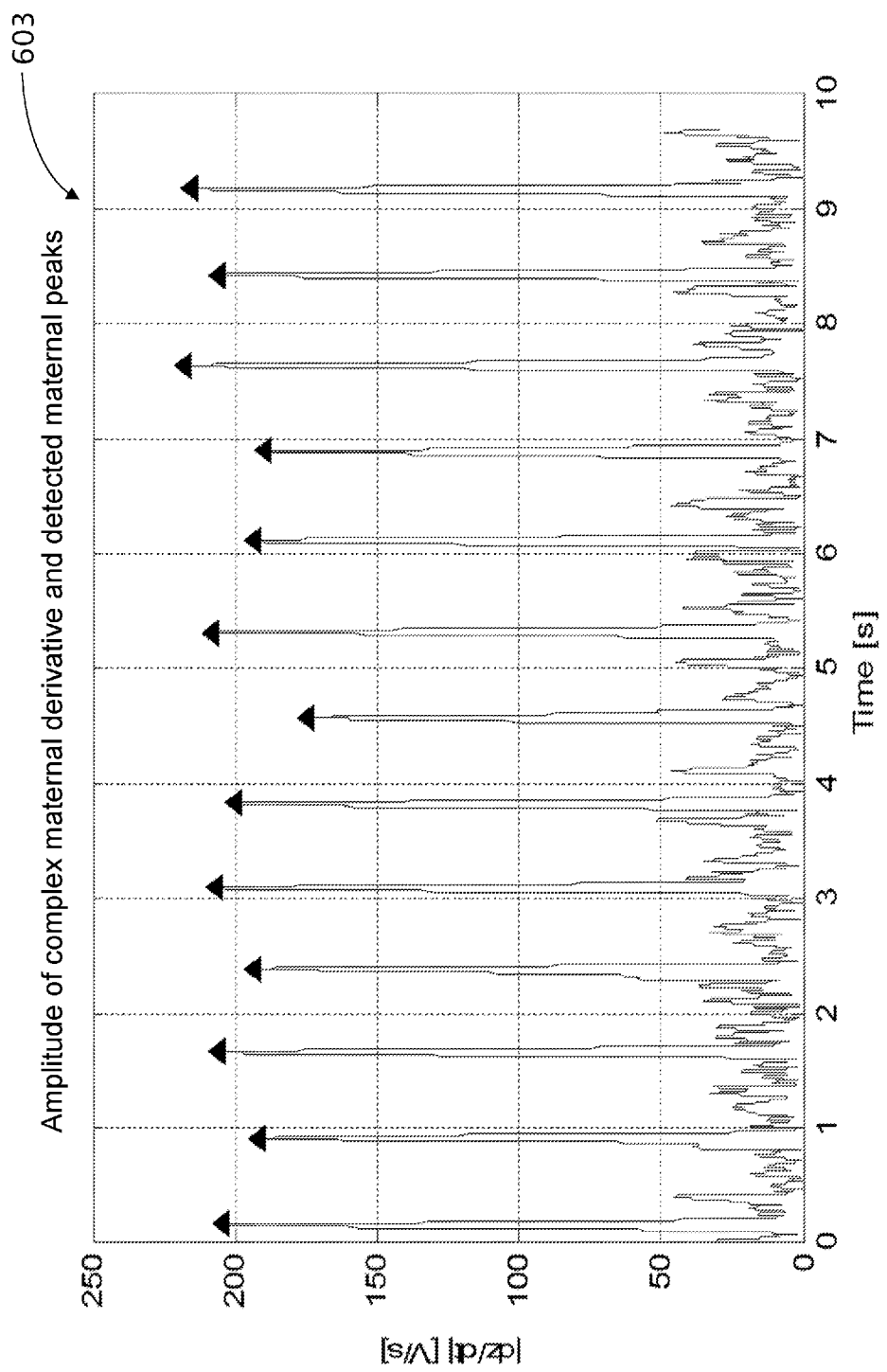
FIG. 10 shows the maternal QRS complexes peaks as detected in the derivative of the summed-up signal, thereby yielding the maternal heart rate.

FIG. 10 shows an example graph 603 of the maternal QRS complexes peaks as detected in the derivative of the summed-up maternal signal, thereby yielding the maternal heart rate. In the example shown, the maternal HR is about 80.

Figure 11:
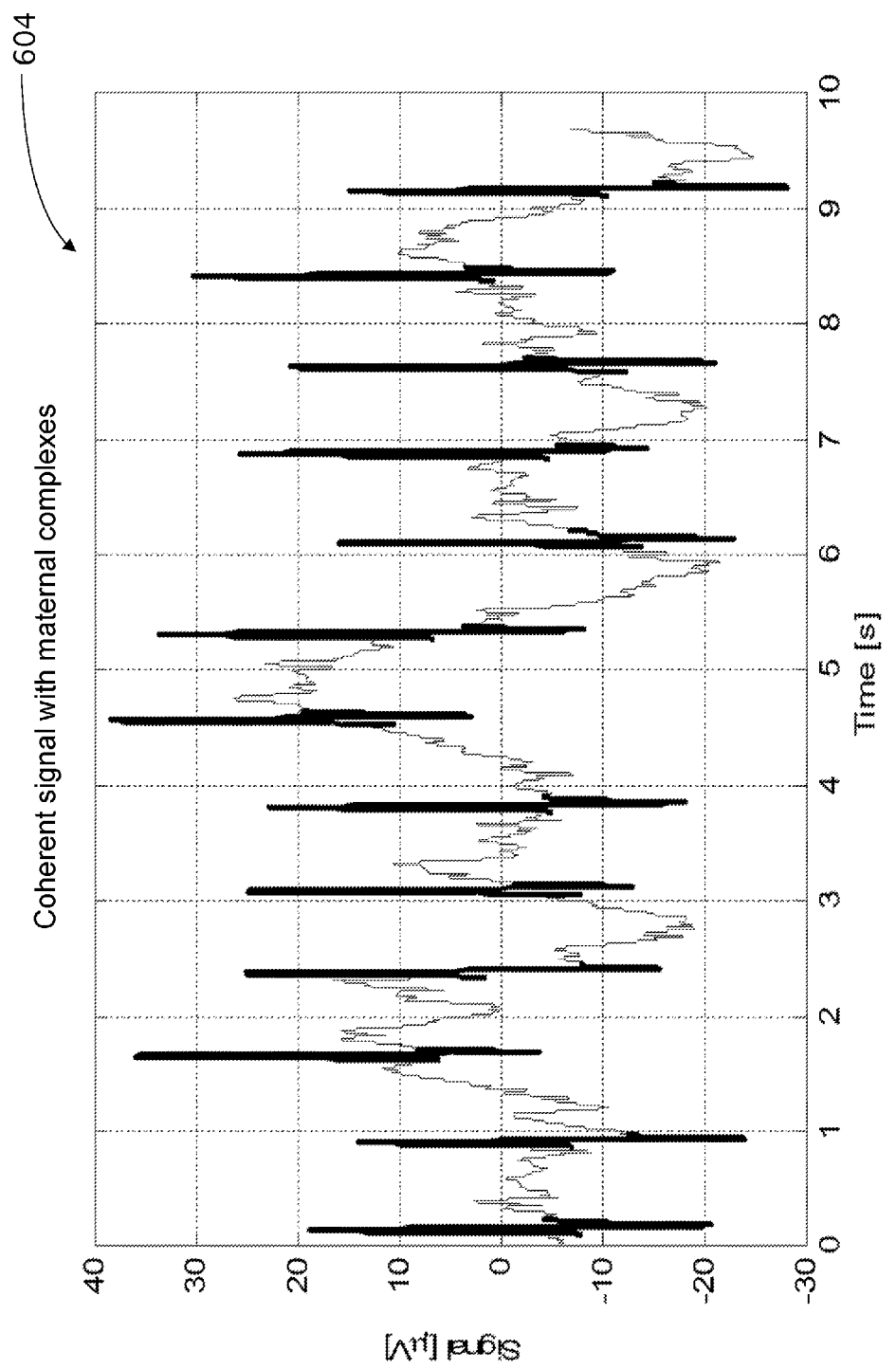
FIG. 11 shows the maternal QRS complexes peaks as overlaid over the summed-up signal.
Figure 12A:
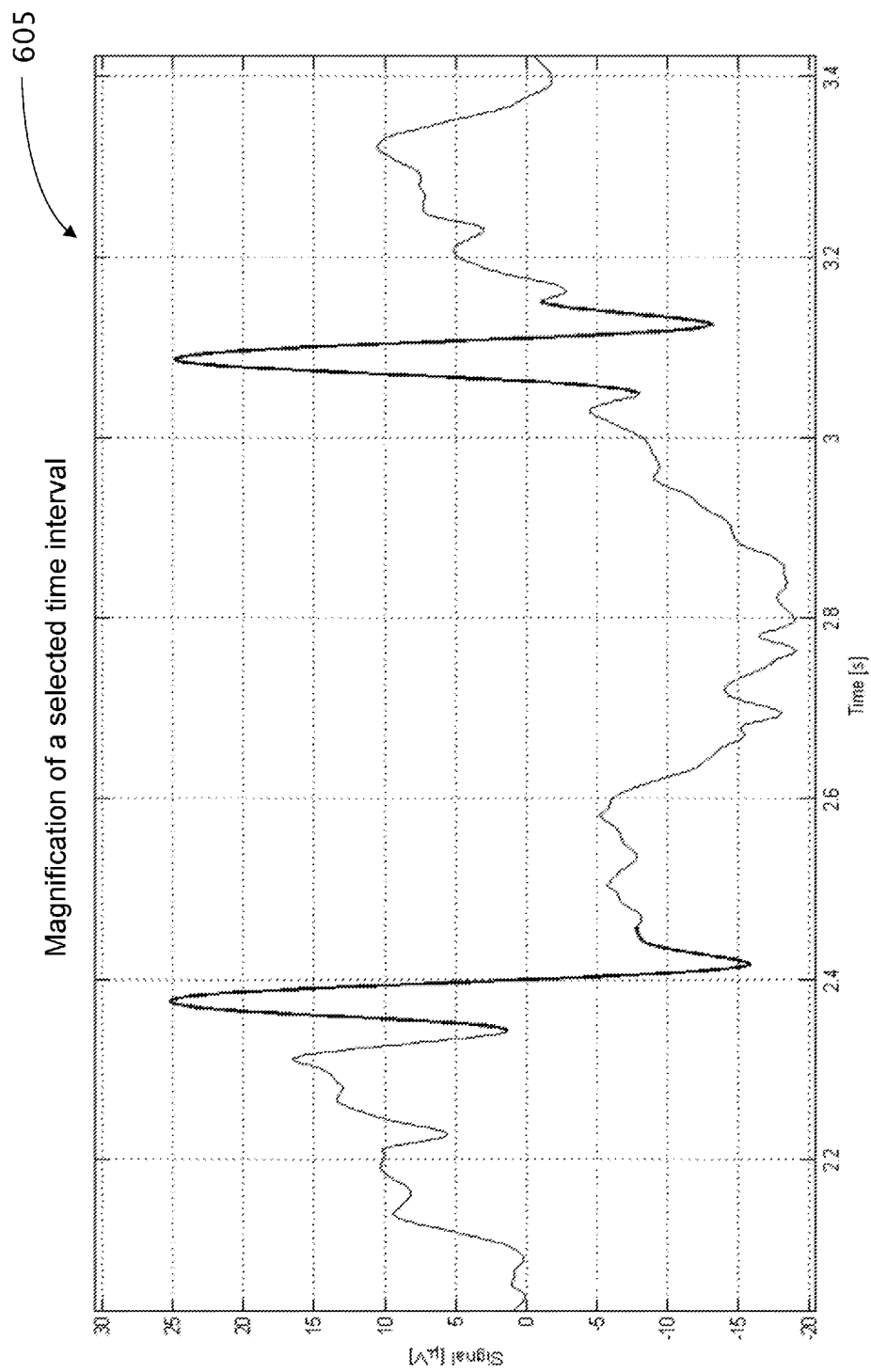
FIG. 12a shows a magnification of a selected time interval of the summed-up signal, as shown in FIG. 11.
Figure 12B:
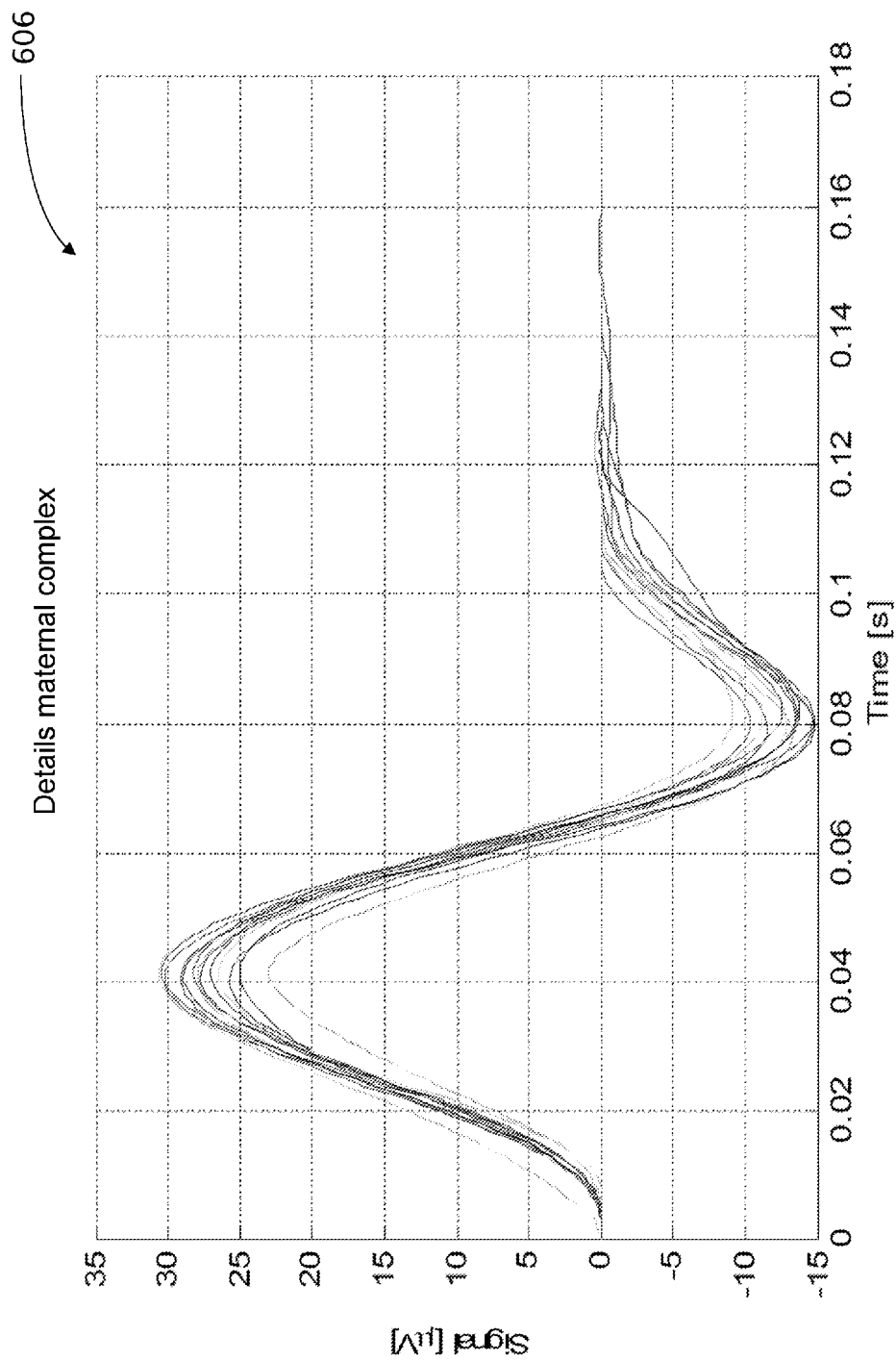
FIG. 12b shows an example maternal QRS complex that can be medically analyzed.

The first and second minimum points of each maternal QRS complex are determined by garment-control device 110, and each maternal QRS complex is disposed in the respective position in each respective filtered ECG signal. FIG. 11 shows an example graph 604 of the maternal QRS complexes as overlaid over the summed-up maternal signal. FIG. 12a shows a magnification 605 of a selected time interval of the summed-up maternal signal, as shown in FIG. 11, and FIG. 12b shows an example graph 606 of a maternal QRS complex that can be medically analyzed. After the QRS complexes peaks are identified and localized, each QRS complex can be analyzed, for example morphologically, and their parameters can be evaluated using methods that cause only slight distortion.

{end of example}

Once the maternal QRS complexes have been found and analyzed, they can be removed either from each of the sensed mixed ECG raw signals or each of the filtered signals. Once removed, a similar process can be executed in order to detect and analyze the fetal QRS complexes.

Figure 13:
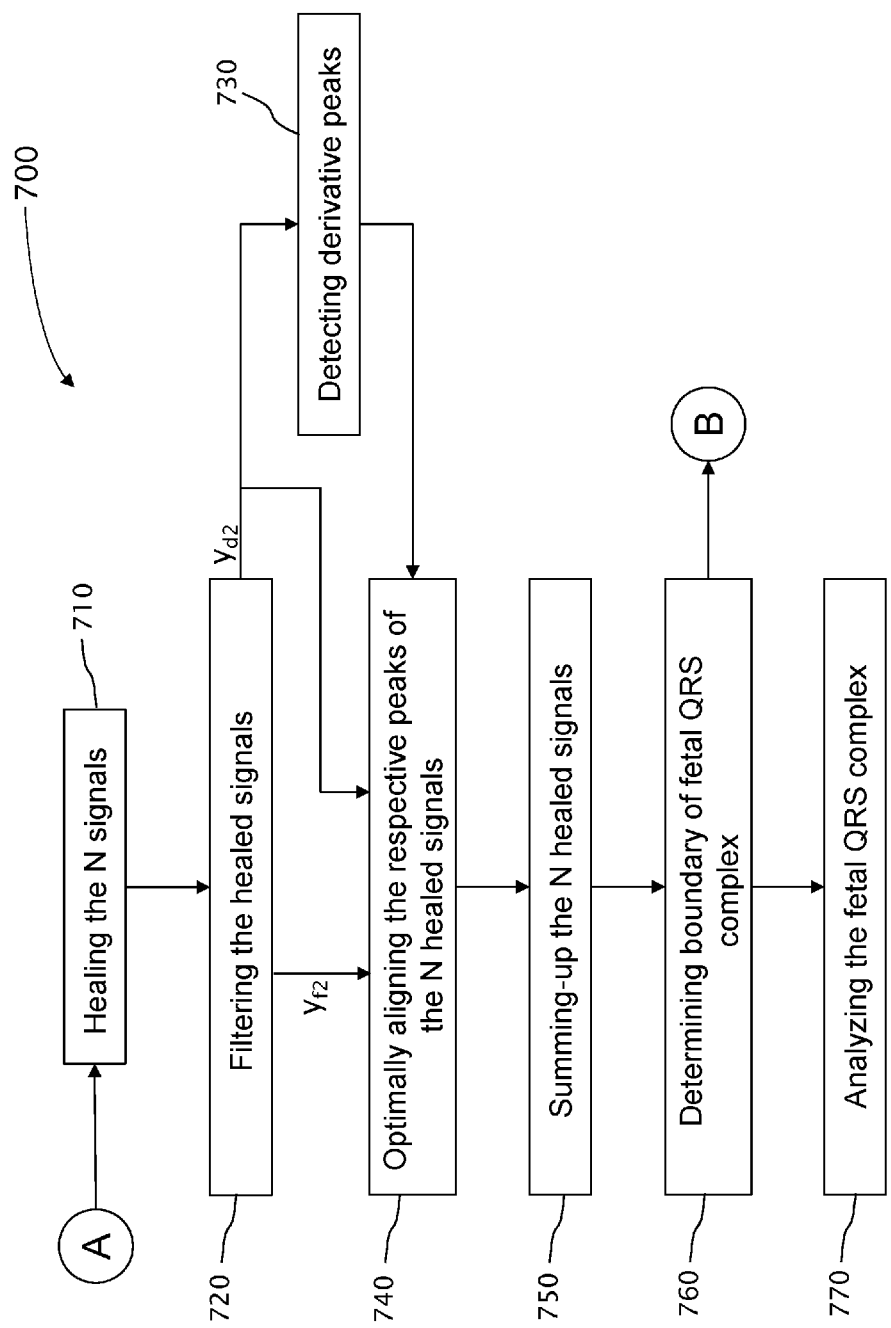
FIG. 13 is a schematic flowchart diagram outlining an example method for detecting, separating and analyzing the fetal QRS signals.

Reference is also made to FIG. 13, showing a schematic flowchart diagram 700 outlining an example method for detecting, separating and analyzing a fetal QRS signal from a multiplicity of simultaneously sensed mixed ECG signals. To begin with, steps 610-660 of method 600 are performed. Then, the overlaid maternal QRS complexes, as respectively overlaid over summed-up ECG signal, as shown in FIG. 11, removed from the respective raw ECG signals, in a process referred to herein as healing, as described here below.

Hence, after steps 610-660 of method 600 are performed, method 700 proceeds with the following steps:

Step 710: healing the N filtered ECG signals.

Garment-control device 110 deletes the maternal QRS complexes from the respective raw ECG signals leaving a gap therein. The gaps formed may be filled by linear interpolation, spline or any other known method. The deleting of QRS complexes from respective raw ECG signals and then filling the gaps formed, is referred to herein as a healing process. A signal yield from the healing process of this step is referred to as a healed-maternal ECG signal.

Step 720: filtering the acquired signals.

Each healed-maternal ECG signal is preferably filtered to substantially reduce the noise. To substantially improve the signal flatness, polynomial filtering may be used, wherein each healed-maternal ECG signal is approximated by a polynomial and its derivative can be evaluated analytically. In some embodiments the polynomial filtering method combines Savitzky-Golay filtering and smoothing spline. Typically, with no limitations, the filtering of each healed-maternal ECG signal yields to signals: $y_{d2}$, a derivative signal that contains the QRS complexes peaks data; and $y_{f2}$, representing the filtered signal.

Step 730: detecting derivative peaks.

Using the derivative signal $y_{d2}$, garment-control device 110 detects derivative peaks that correspond to the fetal QRS complexes peaks of the respective healed-maternal ECG signal.

Step 740: Optimally aligning the respective peaks of the N signals.

Garment-control device 110 reads all filtered healed mixed signals $y_{f2}$ and respective derivative healed signals $y_{d2}$, makes (optionally) an initial sorting of the multiplicity of signals, and optimally calculates the best fetal QRS peaks alignment of the healed-maternal ECG signals. Thereby, the phase shift of each healed-maternal ECG signal is obtained.

To improve phase alignment process an analytical (complex) signal, such as Hilbert transform, may be used.

Step 750: summing-up the N signals.

Garment-control device 110 performs a weighted summing-up of the filtered healed signals, after shifting each filtered mixed signal by the respective calculated phase shift, thereby forming a summed-up coherent fetal signal having a substantially higher SNR than either of the healed-maternal ECG signal.

Step 760: determining the boundary of fetal QRS complexes.

Normally, each QRS complex starts from a first minimum point, reaches maximum and ends at a second minimum point. The first and second minimum points of each QRS complex are determined by garment-control device 110.

Step 770: analyzing the fetal QRS complexes.

Garment-control device 110 analyzes, for example by performing a morphologically analysis, and to determine the fetal HR and possibly detect health hazardous data.

{end of steps details of process 700}

Example

Figure 14:
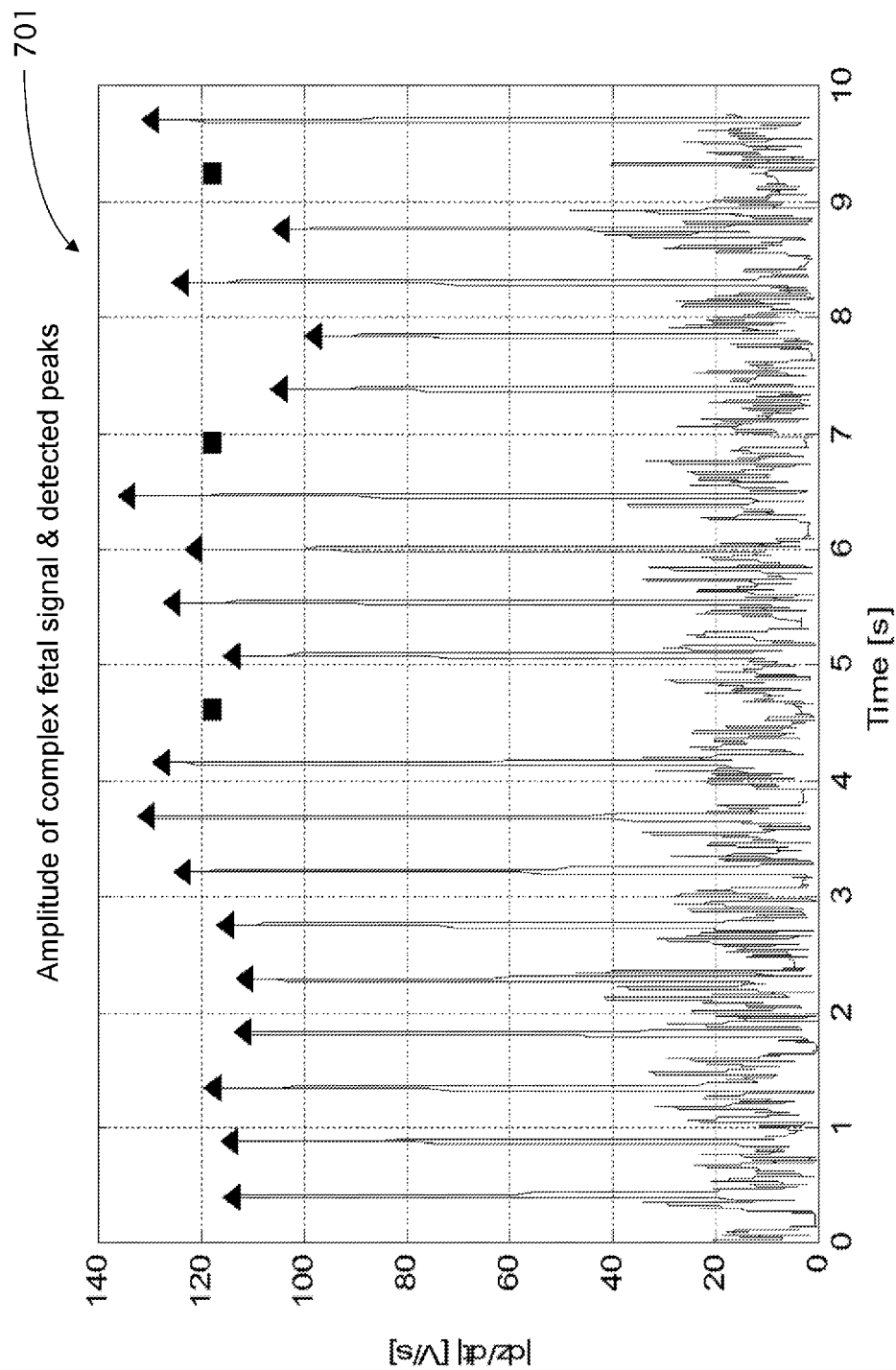
FIG. 14 shows the fetal QRS complexes peaks as detected in the derivative of the summed-up coherent fetal signal, thereby yielding the heart rate of the fetus.

Continuing from the maternal example, reference is also made to FIG. 14, showing an example graph 701 of the fetal QRS complexes peaks as detected in the derivative of the summed-up coherent fetal signal, thereby yielding the fetal heart rate.

Figure 15:
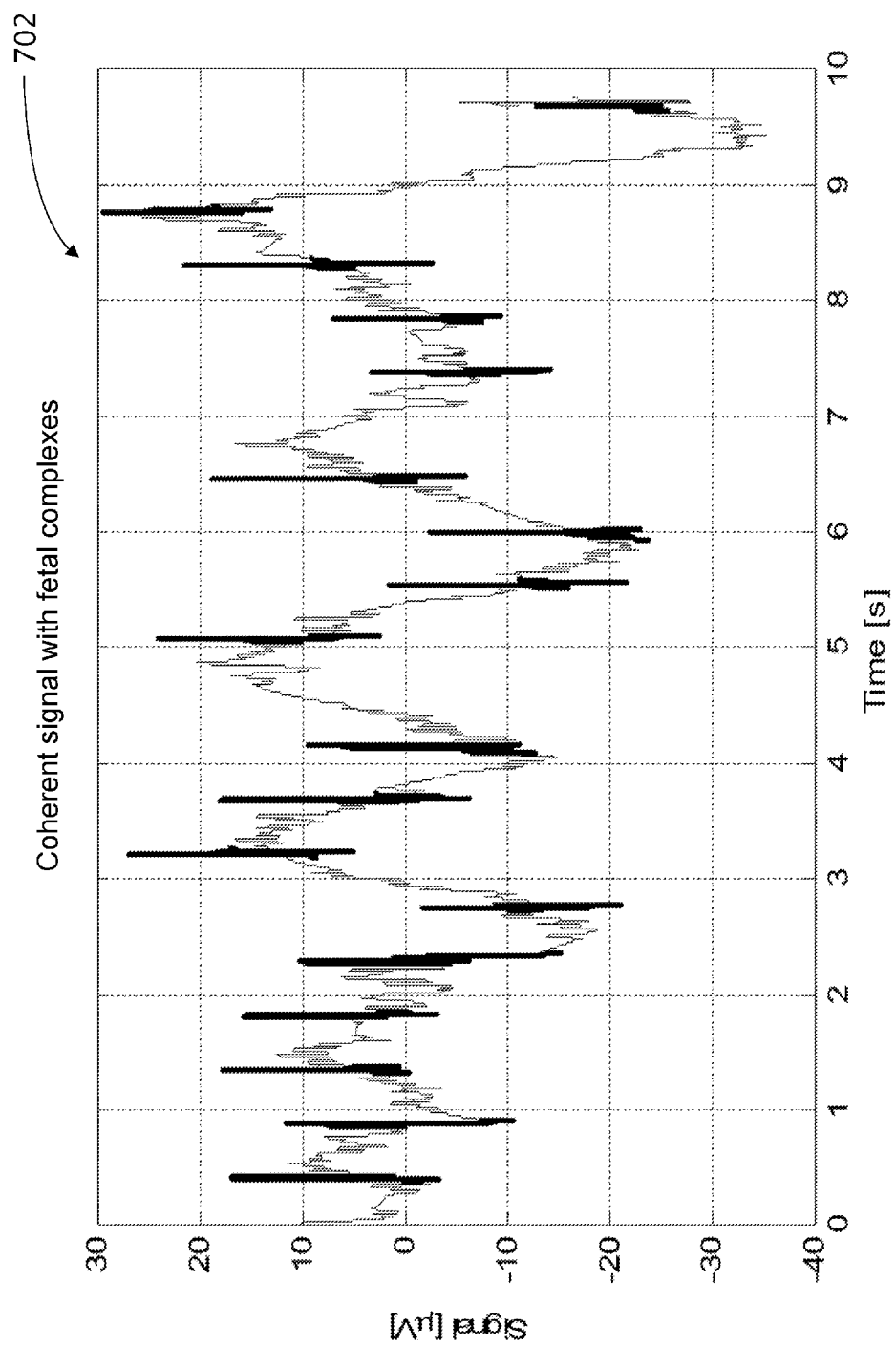
FIG. 15 shows the fetal QRS complexes peaks as overlaid over one of the summed-up coherent fetal signal.

The first and second minimum points of each fetal QRS complex are determined by garment-control device 110, and each fetal QRS complex is disposed in the respective position in each respective filtered ECG signal. FIG. 15 shows an example graph 702 of the fetal QRS complexes as overlaid over one of the four signals composing the healed-maternal ECG signal.

{end of example}

Figure 16:
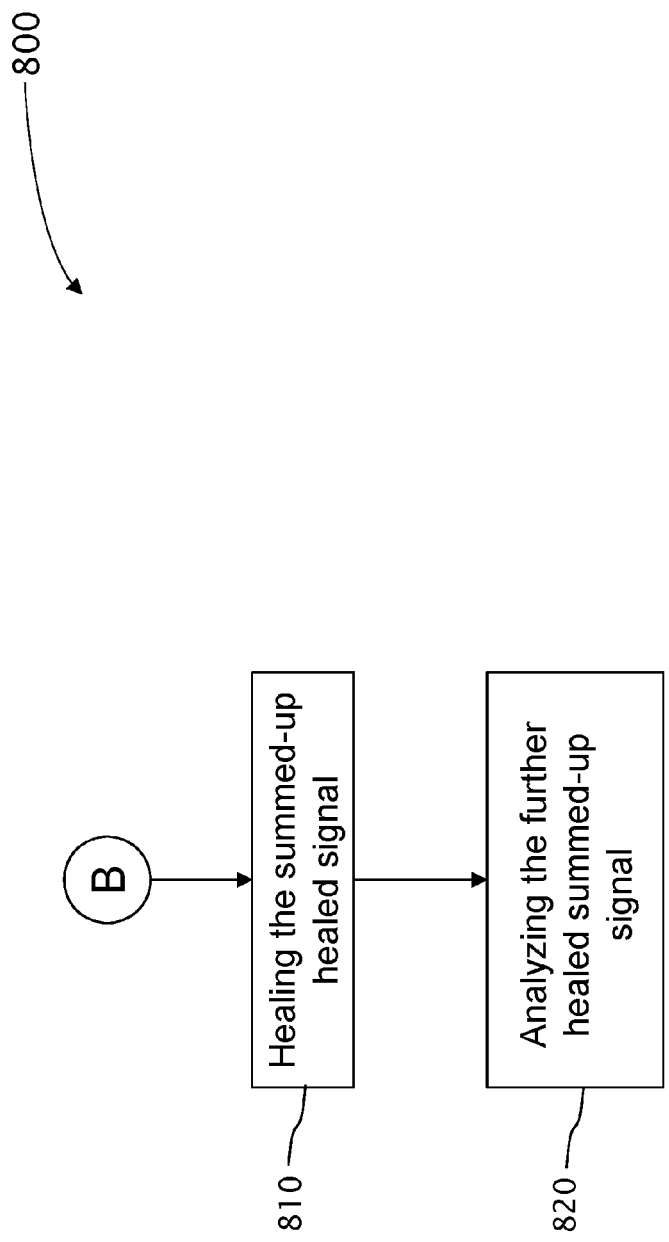
FIG. 16 is a schematic flowchart outlining an example method for detecting and analyzing an EMG signal.

Reference is also made to FIG. 16, showing a schematic flowchart diagram 800 outlining an example method for detecting and analyzing muscles contraction such as uterine contractions, herein referred to as EMG signal analysis. To begin with, steps 610-660 of method 600 and 710-760 of method 700 are performed. Then, method 800 proceeds with the following steps:

Step 810: healing the summed-up coherent fetal signal.

Garment-control device 110 deletes the fetal QRS complexes from the summed-up coherent fetal signal, for example, leaving a gap therein. The gaps formed may be filled by linear interpolation, spline or any other known method. A signal yield from the healing process of this step is referred to as an EMG signal.

Step 820: analyzing the EMG signal.

Garment-control device 110 analyzes, for example by performing a morphologically analysis, and to determines if the uterine is contracting at a rate and amplitude that requires hospitalization for birth giving.

(end of steps details of process 800)

Preferably the health monitoring and self-alert system, including monitoring garment 100, complies with to the IEEE 802.15 standard or an updated standard and FCC Medical Body Area Network (MBAN) systems or an updated standard.

It should be further noted that the monitoring of the health condition is configured to perform continuously. Personal-alerts may be generated immediately as a dangerous situation is detected. The user does not have to perform any activity action in order to get the alert. For the sake of clarity, activity may be required at installation time, but not during monitoring.

It should be further noted that personal-alerts can be issued to the monitored being and/or to an external entity, such as an emergency center, a close relative, etc. The personal-alert can be transmitted to a computer, a telephone and/or any other communication device.

In variation if the present invention, the monitoring garment (200, 202, 204 or 400) includes a generally vertical zipper (not shown), wherein textile electrodes 210 are knitted therein and are individually operatively connected to garment-control device 110. However, some electrodes may require crossing the zipper. To overcome the problem conductive stripes or line traces 220 are knitted into or attached to smart garment 220 in a path that is set to continuously pass through the continuous section of the garment between the two unzipped parts of the zipper.

It should be further noted that the health monitoring and self-alert system can optionally send the data to any remote processor, which can further process the information, compare it to many other monitored people, make statistics-based decisions and other decision-making methods to improve alerts sensitivity and specificity and providing information for the treatment of the living being once getting to a treating facility.

The invention being thus described in terms of embodiments and examples, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for maternal and fetal monitoring comprising the steps of:
   a) wearing a knitted or interwoven smart maternal garment having a plurality of textile electrodes integrally knitted or interwoven therein, said textile electrodes being in communication flow with a processor;
   b) acquiring electrical mixed common, maternal and fetal electrical vital signals from a predetermined external surface region of a pregnant woman, using a plurality of textile electrodes integrally knitted or interwoven into a maternal garment;
   c) optimally weighted summing-up said acquired mixed maternal and fetal electrical vital signals to thereby form a summed-up maternal signal, having a substantially higher SNR than either of the acquired maternal and fetal electrical vital signals;
   d) analyzing the summed-up maternal signal to thereby extract the maternal signal from said summed-up maternal signal; and
   e) healing the acquired mixed maternal and fetal electrical vital signals, including deleting the extracted maternal signal from the respective acquired mixed maternal and fetal electrical vital signal, to thereby form a plurality of healed-maternal ECG signals;
   f) optimally weighted summing-up said healed-maternal ECG signals to thereby form a summed-up coherent fetal signal, having a substantially higher SNR than either of the healed-maternal ECG signals;
   g) analyzing said summed-up coherent fetal signal to thereby extract a fetal signal from said summed-up coherent fetal signal.

2. The method of claim 1 further comprising the step of:
   h) analyzing said summed-up coherent fetal signal thereby extract the EMG signal formed by electromyogram (EMG) activities including uterine activities, from said summed-up coherent fetal signal.

3. The method of claim 2, wherein said extracting and analyzing of said EMG signal from said summed-up electrical signal comprises the steps of:
   a) detecting the peaks in the maternal QRS complexes in said summed-up maternal signal;
   b) determining the boundary of each said detected maternal QRS complex;
   c) deleting each said detected maternal QRS complex from the respective acquired mixed maternal and fetal electrical vital signal and filling the gap formed therein, thereby forming a respective healed-maternal ECG signal;
   d) detecting the peaks of fetal QRS complexes in said summed-up coherent fetal signal;
   e) determining the boundary of each said detected fetal QRS complex;
   f) deleting each said detected fetal QRS complex from the summed-up coherent fetal signal and filling the gap formed therein, thereby forming a EMG summed-up signal; and
   g) analyzing the EMG summed-up signal.

4. The method of claim 3, wherein said analysis of said EMG summed-up signal includes performing a morphologically analysis to thereby determine if the uterine is contracting at a rate and amplitude that requires hospitalization for birth giving.

5. The method of claim 3, wherein said filling of said gap includes by using linear interpolation or spline.

6. The method of claim 1, wherein said extracting and analyzing of said maternal signal from said summed-up electrical signal comprises the steps of:
   a) detecting the peaks in the maternal QRS complexes using said summed-up maternal signal, the maternal QRS complexes peaks being substantially stronger than the fetal QRS complexes;
   b) determining the boundary of each said detected maternal QRS complex;
   c) analyzing said summed-up maternal signal to thereby extract said maternal signal and determine the maternal HR; and
   d) analyzing each said detected maternal QRS complex to thereby detect health hazardous data.

7. The method of claim 1, wherein said extracting and analyzing of said fetal signal from said summed-up electrical signal comprises the steps of:
   a) detecting the peaks in the maternal QRS complexes in said summed-up maternal signal, the maternal QRS complexes peaks being substantially stronger than the fetal QRS complexes;
   b) determining the boundary of each said detected maternal QRS complex;
   c) deleting each said detected maternal QRS complex from the respective said acquired mixed maternal and fetal electrical vital signal and filling the gap formed therein, thereby forming a respective healed-maternal ECG signal;
   d) optimally-weighted summing-up said healed-maternal ECG signals to thereby form a summed-up coherent fetal signal, having a substantially higher SNR than either of said healed-maternal ECG signals;
   e) detecting the peaks of fetal QRS complexes in said summed-up coherent fetal signal;
   f) determining the boundary of each said detected fetal QRS complex;
   g) analyzing said summed-up maternal signal to thereby extract said fetal signal and determine the fetal HR; and
   h) analyzing each said detected fetal QRS complex to thereby detect health hazardous data.

8. The method of claim 7, wherein said filling of said gap includes by using linear interpolation or spline.

9. The method of claim 7, wherein said summed-up coherent fetal signal contains more than one fetus and wherein said fetal QRS complexes of the signal of each fetus is separated based on different heart rate and/or different phase normal or inverted QRS Complex.

10. The method of claim 9, wherein said separation of the signal of each fetus is performed using Fourier transform.

11. The method of claim 1, wherein said maternal garment is worn without attaching either of said electrodes,
- regardless of the precise bodily positioning of each said electrode;
- regardless of the chronological stage of the pregnancy; and
- regardless of the amount of stretching of the tubular form and of each said electrode.

12. The method of claim 1, wherein said maternal signal includes maternal heart rate.

13. The method of claim 1, wherein said fetal signal includes fetal heart rate.

14. The method of claim 1, wherein said predetermined external surface region is selected from a group including the abdomen, the perineum and buttocks of said pregnant woman.

15. The method of claim 1, wherein said conductive textile electrodes include a preconfigured number of measuring electrodes and a preconfigured number of reference electrodes.

16. The maternal garment of claim 15, wherein each said measuring electrode is paired with at least one reference electrode.

17. The method of claim 15, wherein each given said conductive textile electrode, in a specific measurement instance, is paired with a preconfigured number of other said conductive textile electrodes, and wherein in each said pairing, said given conductive textile electrode serves either as a measuring electrode or as a reference electrode, thereby facilitating increasing the number of differential measurements acquired, in said specific measurement instance, beyond said second multiplicity of said conductive textile electrodes.

18. The method of claim 15, wherein said measuring electrodes and said reference electrodes are positioned, within the maternal garment, in preconfigured locations.

19. The method of claim 18, wherein said position of said measuring electrodes and said reference electrodes are preconfigured to thereby optimize the spatial coverage of the uterine.

20. The method of claim 15, wherein the pairing of said measuring electrodes and respective said reference electrodes are preset using said processor.

21. The method of claim 20, wherein said number of measuring electrodes, said number of reference electrodes and said pairing thereof are preset to thereby optimize the signal to noise (SNR) ratio.

* * * * *